(12) United States Patent
Mitragotri et al.

(10) Patent No.: US 11,684,594 B2
(45) Date of Patent: Jun. 27, 2023

(54) ANTIFUNGAL PROPHYLAXIS FOR CORNEA

(71) Applicant: PRESIDENT AND FELLOWS OF HARVARD COLLEGE, Cambridge, MA (US)

(72) Inventors: Samir Mitragotri, Lexington, MA (US); Eden E. L. Tanner, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 17/318,048

(22) Filed: May 12, 2021

(65) Prior Publication Data
US 2021/0353565 A1 Nov. 18, 2021

Related U.S. Application Data

(60) Provisional application No. 63/023,374, filed on May 12, 2020.

(51) Int. Cl.
*A61K 31/14* (2006.01)
*A61K 9/00* (2006.01)
*A61P 31/00* (2006.01)
*A61K 45/06* (2006.01)

(52) U.S. Cl.
CPC ............ *A61K 31/14* (2013.01); *A61K 9/0048* (2013.01); *A61K 45/06* (2013.01); *A61P 31/00* (2018.01)

(58) Field of Classification Search
CPC ...... A61K 31/14; A61K 9/0048; A61K 31/20; A61P 31/00
See application file for complete search history.

(56) References Cited

U.S. PATENT DOCUMENTS

| 5,124,061 A | 6/1992 | Geary, Sr. |
| 2004/0253747 A1 | 12/2004 | Ponzoni et al. |
| 2015/0071922 A1 | 3/2015 | Larson et al. |
| 2015/0164828 A1 | 6/2015 | Golini |
| 2015/0328113 A1 | 11/2015 | Patel et al. |
| 2016/0263225 A1 | 9/2016 | Zakrewsky et al. |
| 2018/0093011 A1 | 4/2018 | Kellar et al. |

FOREIGN PATENT DOCUMENTS

| CN | 106420610 A | 2/2017 |
| CN | 109464661 A | 3/2019 |
| KR | 20170052278 A | 5/2017 |
| WO | 2004052340 A1 | 6/2004 |
| WO | 2015066647 A2 | 5/2015 |
| WO | 2016054259 A1 | 4/2016 |
| WO | 2017164627 A2 | 9/2017 |
| WO | 2018044920 A1 | 3/2018 |
| WO | 2018222924 A1 | 12/2018 |
| WO | 2019099837 A1 | 5/2019 |
| WO | 2019122329 A1 | 6/2019 |
| WO | 2019183142 A1 | 9/2019 |
| WO | 2019201894 A1 | 10/2019 |
| WO | 2019217854 A1 | 11/2019 |
| WO | 2021092522 A1 | 5/2021 |

OTHER PUBLICATIONS

Paul et al., "Deciphering the interaction of a model transport protein with a prototypical imidazolium room temperature ionic liquid: effect on the conformation and activity of the protein." Journal of Photochemistry and Photobiology B: Biology 133:99-107 (2014).
Petkovic et al. "Novel biocompatible cholinium-based ionic liquids—toxicity and biodegradability." Green Chemistry 12(4): 643-649 (2010).
Qi et al. "Mechanistic study of transdermal delivery of macromolecules assisted by ionic liquids." Journal of Controlled Release 311: 162-169 (2019).
Rogers et al., "Ionic liquids—solvents of the future?," Science 302(5646):792-793 (2003).
Sahbaz et al., "Transformation of poorly water-soluble drugs into lipophilic ionic liquids enhances oral drug exposure from lipid based formulations." Molecular Pharmaceutics 12(6):1980-1991 (2015).
Shamshina et al., "Ionic liquids in drug delivery." Expert Opinion on Drug Delivery 10(10):1367-1381 (2013).
Shao "On the influence of hydrated imidazolium-based ionic liquid on protein structure stability: a molecular dynamics simulation study." The Journal of Chemical Physics 139(11):115102 (2013).
Shi et al. "Oral delivery of sorafenib through spontaneous formation of ionic liquid nanocomplexes." Journal of Controlled Release 322: 602-609 (2020).
Singh et al., "Dynamics of ionic liquid-assisted refolding of denatured cytochrome c: a study of preferential interactions toward renaturation." Molecular Pharmaceutics 15(7):2648-2697 (2018).
Singh et al., "Effect of polysorbate 20 and polysorbate 80 on the higher-order structure of a monoclonal antibody and its Fab and Fc fragments probed using 2D nuclear magnetic resonance spectroscopy." Journal of Pharmaceutical Sciences 106(12):3486-3498 (2017).
Sivapragasam et al., "Recent advances in exploiting ionic liquids for biomoiecules: solubility, stability and applications." Biotechnology Journal 11(8):1000-1013 (2016).
Stärtzel "Arginine as an excipient for protein freeze-drying: A mini review," Journal of Pharmaceutical Sciences 107(4):960-967 (2018).
Streit et al., "Topical application of the tumour necrosis factor-α antibody infliximab improves healing of chronic wounds." International Wound Journal 3(3):171-179 (2006).
Tanner et al. "Design principles of ionic liquids for transdermal drug delivery." Advanced Materials 31(27): 1901103 pp. 1-10 (2019).
Tanner et al., "Transdermal insulin delivery using choline-based ionic liquids (CAGE)" Journal of Controlled Release 286:137-144 (2018).
Uralcan et al. "A computational study of the ionic liquid-induced destabilization of the miniprotein, Trp-Cage." The Journal of Physical Chemistry B 122(21):5707-5715 (2018).

(Continued)

*Primary Examiner* — Sahar Javanmard
(74) *Attorney, Agent, or Firm* — Nixon Peabody LLP; David S. Resnick; Nicole D. Kling

(57) ABSTRACT

The technology described herein is directed to ionic liquids for using the treatment or prevention of fungal infections.

17 Claims, 6 Drawing Sheets

(56) References Cited

OTHER PUBLICATIONS

Veselinovic et al., "Topical gel formulation of broadly neutralizing anti-HIV-1 monoclonal antibody VRC01 confers protection against HIV-1 vaginal challenge in a humanized mouse model." Virology 432(2):505-510 (2012).

Vllasaliu et al. "Recent advances in oral delivery of biologies: Nanomedicine and physical modes of delivery." Expert opinion on drug delivery 15(8): 759-770 (2018).

Wang et al., "Stabilizing two IgG1 monoclonal antibodies by surfactants: Balance between aggregation prevention and structure perturbation." European Journal of Pharmaceutics and Biopharmaceutics 114:263-277 (2017).

Wei, et al. "Biomimetic Micromotor Enables Active Delivery of Antigens for Oral Vaccination." Nano letters 19(3):1914-1921 (2019).

Williams et al., "Ionic liquids provide unique opportunities for oral drug delivery: structure optimization and in vivo evidence of utility." Chemical Communications 50(14):1688-1690 (2014).

Wu et al. "Improving dermal delivery of hydrophilic macromolecules by biocompatible ionic liquid based on choline and malic acid." Int J Pharm 558: 380-387 (2019).

Yang et al., "Using ionic liquids in whole-cell biocatalysis for the nucleoside acylation." Microbial Cell Factories 13(1):143 (2014).

Zakrewsky et al., "Choline and geranate deep eutectic solvent as a broad-spectrum antiseptic agent for preventive and therapeutic applications." Advanced Healthcare Materials 5(11):1282-1289 (2016).

Zakrewsky et al., "Ionic liquids as a class of materials for transdermal delivery and pathogen neutralization." PNAS 111(37):13313-13318 (2014).

Zeisel. "Choline: Human requirements and effects on human performance." In Food Components to Enhance Performance: An Evaluation of Potential Performance-Enhancing Food Components for Operational Rations. Institute of Medicine, Committee on Military Nutritional Research Food and Nutrition Board, B. M. Marriott, Ed. National Academies Press, Washington DC. Chapter 19: 381-406 (1994).

Zhang et al. "Evaluations of imidazolium ionic liquids as novel skin permeation enhancers for drug transdermal delivery." Pharm Dev Technol 22(4): 511-520 (2017).

Zhang et al., "Impact of the alkyl chain length on binding of imidazolium-based ionic liquids to bovine serum albumin." Spectrochimica Acta Part A: Molecular and Biomolecular Spectroscopy 196:323-333 (2018).

Abbott et al., "Deep eutectic solvents formed between choline chloride and carboxylic acids: versatile alternatives to ionic liquids." Journal of the American Chemical Society 126(29):9142-9147 (2004).

Adawiyah et al., "Ionic liquids as a potential tool for drug delivery systems." MedChemComm 7(10):1881-1897 (2016).

Agatemor et al., "Ionic liquids for addressing unmet needs in healthcare." Bioengineering & Translational Medicine 3(1):7-25 (2018).

Ammendola et al. "10-Undecanhydroxamic acid, a hydroxamate derivative of the undecanoic acid, has strong antimicrobial activity through a mechanism that limits iron availability." FEMS Microbiology Letters 294(1): 61-67 (2009).

Araki et al. "Ionic liquid-mediated transcutaneous protein delivery with solid-in-oil nanodispersions." MedChemComm 6(12): 2124-2128 (2015).

Banerjee et al. "Ionic liquids for oral insulin delivery." PNAS 115(28): 7296-7301 (2018).

Banerjee et al., "Transdermal protein delivery using choline and geranate (CAGE) deep eutectic solvent." Advanced Healthcare Materials 6(15):1601411 (2017).

Bergsson et al. "in vitro killing of Candida albicans by fatty acids and monoglycerides." Antimicrobial Agents and Chemotherapy 45(11): 3209-3212 (2001).

Berton et al. "Transdermal Bioavailability in Rats of Lidocaine in the Forms of Ionic Liquids, Salts, and Deep Eutectic." ACS Med Chem Lett 8(5): 498-503 (2017).

Carrillo-Conde et al. "Complexation hydrogels as oral delivery vehicles of therapeutic antibodies: an in vitro and ex vivo evaluation of antibody stability and bioactivity." Industrial & engineering chemistry research 54(42): 10197-10205 (2015).

Chen et al. "Enhanced paracellular delivery of vaccine by hydrogel microparticles-mediated reversible tight junction opening for effective oral immunization." Journal of Controlled Release 311-312: 50-64 (2019).

De Ávila et al. "Micromotor-enabled active drug delivery for in vivo treatment of stomach infection," Nature communications 8(1): 272 pp. 1-9 (2017).

Dharamdasani et al. "Topical delivery of siRNA into skin using ionic liquids." Journal of Controlled Release 323: 475-482 (2020).

Dobler et al. "Ionic liquids as ingredients in topical drug delivery systems." International Journal of Pharmaceutics 441(1-2): 620-627 (2013).

Egorova et al., "Biological activity of ionic liquids and their application in pharmaceutics and medicine." Chemical Reviews 117(10):7132-7189 (2017).

Esteban-Fernández De Ávila et al. "Micromotors go in vivo: from test tubes to live animals." Advanced Functional Materials 28(25): 1705640 (2018).

Fan et al. "Functional nanoparticles exploit the bile acid pathway to overcome multiple barriers of the intestinal epithelium for oral insulin delivery." Biomaterials 151: 13-23 (2018).

Fiebig et al., "Quantitative evaluation of myoglobin unfolding in the presence of guanidinium hydrochloride and ionic liquids in solution." The Journal of Physical Chemistry B 118(2):406-412 (2013).

Goindi et al. "Development of novel ionic liquid-based microemulsion formulation for dermal delivery of 5-fluorouracil." AAPS PharmSciTech 15(4): 810-821 (2014).

Haidar et al., "Development of topical delivery systems for flightless neutralizing antibody." Journal of Pharmaceutical Sciences 106(7):1795-1804 (2017).

Hsu et al. "Delivery of siRNA and other macromolecules into skin and cells using a peptide enhancer." Proceedings of the National Academy of Sciences 108(38): 15816-15821 (2011).

Ibsen et al., "Mechanism of antibacterial activity of choline-based ionic liquids (CAGE)." ACS Biomaterials Science & Engineering 4(7): 2370-2379 (2018).

Jain et al., "Effect of trehalose on protein structure." Protein Science 18(1):24-36 (2009).

Jean. "Esters et sels de la choline et de quelues acides derives du phosphore." Bulletin de la Societe Chimique de France 5: 783-786 (1957).

Kandimalla et al. "Effect of fatty acids on the permeation of melatonin across rat and pig skin in-vitro and on the transepidermal water loss in rats in-vivo." JPharmPharmacol 51(7): 783-790 (2010).

Karande et al., "Design principles of chemical penetration enhancers for transdermal drug delivery." PNAS 102 (13):4688-4693 (2005).

Karande et al. "Discovery of transdermal penetration enhancers by high-throughput screening." Nature Biotechnology 22(2): 192-197 (2004).

Kelley et al., "Understanding the effects of ionicity in salts, solvates, co-crystals, ionic co-crystals, and ionic liquids, rather than nomenclature, is critical to understanding their behavior." Crystal Growth and Design. 13(3):965-975 (2013).

Khan et al., "Key interactions of surfactants in therapeutic protein formulations: A review." European Journal of Pharmaceutics and Biopharmaceutics 97 97(Pt A):60-67 (2015).

Kharroubi et al., "Diabetes mellitus: The epidemic of the century." World Journal of Diabetes 6(6):850-867 (2015).

Korkmaz et al., "Therapeutic intradermal delivery of tumor necrosis factor-alpha antibodies using tip-loaded dissolvable microneedle arrays." Acta Biomaterialia 24:96-105 (2015).

Korkmaz et al., "Topically applied flightless I neutralizing antibodies improve healing of blistered skin in in a murine model of epidermolysis bullosa acquisita." Journal of Investigative Dermatology 133(4):1008-1016 (2013).

(56) References Cited

OTHER PUBLICATIONS

Kumar et al. "Peptides as skin penetration enhancers: mechanisms of action." Journal of Controlled Release 199:168-178 (2015).

Lane. "Skin penetration enhancers." International Journal of Pharmaceutics 447(1-2): 12-21 (2013).

Lee et al. "Development of pH-responsive organic-inorganic hybrid nanocomposites as an effective oral delivery system of protein drugs." Journal of Controlled Release 311-312: 74-84 (2019).

Lei et al., "Introduction: ionic liquids." Chem Rev 117(10):6633-6635 (2017).

Lesch et al., "Peptides in the presence of aqueous ionic liquids—tunable co-solutes as denaturants or protectants?" Physical Chemistry Chemical Physics 17(39):26049-26053 (2015).

Li et al. "Micromotors Spontaneously Neutralize Gastric Acid for pH-Responsive Payload Release." Angewandte Chemie International Edition 56(8): 2156-2161 (2017).

Li et al., "Insights into the deactivation of bovine serum albumin with a thermo-responsive ionic liquid." Soft Matter 10(33):6161-6171 (2014).

Marrucho et al., "Ionic liquids in pharmaceutical applications." Annual Review of Chemical and Biomolecular Engineering 5:527-546 (2014).

Moniruzzaman et al. "Ionic liquid based microemulsion with pharmaceutically accepted components: Formulation and potential applications." Journal of Colloid and Interface Science 352(1): 136-142 (2010).

Monti et al. "Ionic liquids as potential enhancers for transdermal drug delivery." Int J Pharm 516(1-2): 45-51 (2017).

Muheem et al. "A review on the strategies for oral delivery of proteins and peptides and their clinical perspectives." Saudi Pharmaceutical Journal 24(4): 413-428 (2016).

Nurunnabi et al. "Oral Ionic liquid for the treatment of diet-induced obesity," Proceedings of the National Academy of Sciences 116(50): 25042-25047 (2019).

O'Toole et al. "Diphosphonium ionic liquids as broad spectrum antimicrobial agents." Cornea 31(7): 810-816 (2012).

Park et al. "Lidocaine-ibuprofen ionic liquid for dermal anesthesia." AIChE Journal 61(9): 2732-2738 (2015).

Patel et al., "Recent advances in the applications of ionic liquids in protein stability and activity: a review." Applied Biochemistry and Biotechnology 172(8):3701-3720 (2014).

Hough et al., (The Third Evolution of Ionic Liquids: Active Pharmaceutical Ingredients New Journal of Chemistry 31(8): 1429 (2014).

Zhang et al., "A hydrophobic deep eutectic solvent-based vortex-assisted dispersive liquid-liquid microextraction combined with HPLC for the determination of nitrite in water and biological samples", Journal of Separation Science, vol. 42, No. 2, (Oct. 28, 2018), pp. 574-581.

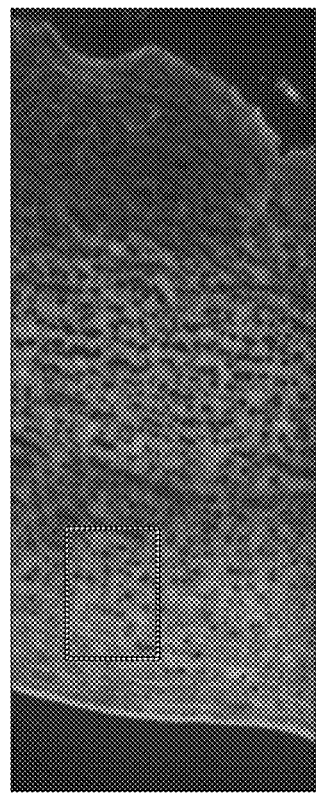
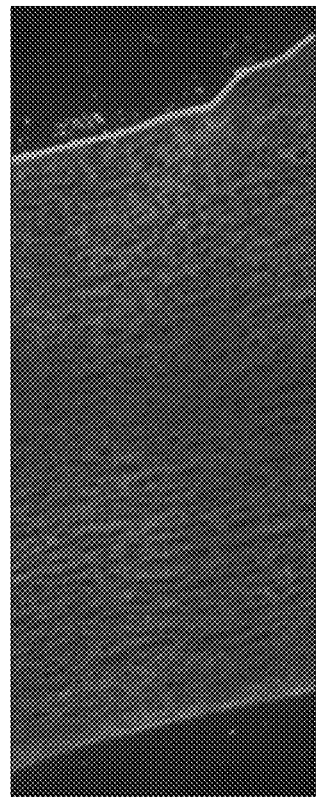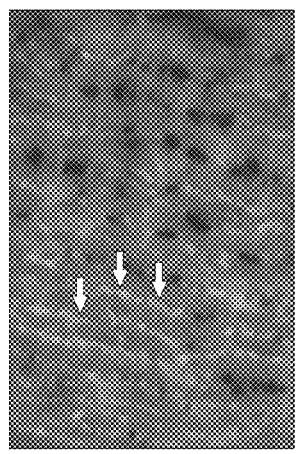
FIG. 6A
FIG. 6B

ANTIFUNGAL PROPHYLAXIS FOR CORNEA

CROSS-REFERENCE TO RELATED APPLICATIONS

This application claims benefit under 35 U.S.C. § 119(e) of U.S. Provisional Application No. 63/023,374 filed May 12, 2020 the contents of which are incorporated herein by reference in their entirety.

TECHNICAL FIELD

The technology described herein relates to ionic liquids, e.g., choline and undecanoic acid for treatment or prevention of fungal infections.

BACKGROUND

After eye surgery, particularly keratoprosthesis (KPro) implantation, subjects can remain extremely susceptible to eye infections for the rest of their life. Daily prophylactic antibiotics are common to prevent bacterial infections, but affordable and tolerable antifungal agents are lacking.

SUMMARY

It is demonstrated herein that the ionic liquid choline:undecanoic acid is surprisingly effective against ocular fungal infections, virtually non-toxic, and both affordable and practical for daily life-long use. The ionic liquid choline:undecanoic acid provides antifungal activity superior to a panel of tested agents, including current clinical standards.

Accordingly, described herein is a composition comprising at least one ionic liquid comprising a quaternary ammonium cation and an undecanoic acid anion. In some embodiments of any of the aspects, the cation has a molar mass equal to or greater than choline. In some embodiments of any of the aspects, quaternary ammonium has the structure of $NR_4^+$ and at least one R group comprises a hydroxy group. In some embodiments of any of the aspects, quaternary ammonium has the structure of $NR_4^+$ and only one R group comprises a hydroxy group. In some embodiments of any of the aspects, the cation is choline, C1, C6, or C7.

In some embodiments of any of the aspects, the ionic liquid is at a concentration of at least 0.1% w/v. In some embodiments of any of the aspects, the ionic liquid is at a concentration of from 10 to 70% w/v. In some embodiments of any of the aspects, the ionic liquid is at a concentration of from 30 to 50% w/v. In some embodiments of any of the aspects, the ionic liquid is at a concentration of from 30 to 40% w/v. In some embodiments of any of the aspects, the ionic liquid comprises a ratio of cation to anion of from 2:1 to 1:10. In some embodiments of any of the aspects, the ionic liquid comprises a ratio of cation to anion of from 2:1 to 1:2. In some embodiments of any of the aspects, the ionic liquid comprises a ratio of cation to anion of from 1:1 to 1:4. In some embodiments of any of the aspects, the ionic liquid has a cation:anion ratio of 1:1.

In some embodiments of any of the aspects, the composition does not comprise an active agent other than the at least one ionic liquid. In some embodiments of any of the aspects, the composition further comprises at least one additional active compound other than the at least one ionic liquid. In some embodiments of any of the aspects, the at least one additional active compound is an additional antifungal agent. In some embodiments of any of the aspects, the one or more additional antifungal agents are selected from the group consisting of: amphotericin B; natamycin; voriconazole; povidone-iodine; hypochlorous acid; Chlorhexidine digluconate (CDG); vancomycin (VAN); chloramphenicol (CHL); polymyxin B (PMB); trimethoprim (TMP); benzalkonium chloride (BAK); and combinations thereof.

In some embodiments of any of the aspects, the composition is formulated for administration transdermally, to a mucus membrane, orally, ocularly, to the cornea, subcutaneously, intradermally, parenterally, intratumorally, or intravenously. In some embodiments of any of the aspects, the composition is formulated for ocular administration.

The compositions described herein can be used to treat or prevent fungal infections. Accordingly, described herein is a method of treating or preventing a fungal infection, comprising administering to a subject in need thereof a composition described herein. In some embodiments of any of the aspects, the administration is transdermal, to a mucus membrane, oral, subcutaneous, intradermal, parenteral, intratumoral, ocular, or intravenous. In some embodiments of any of the aspects, the fungal infection is an ocular fungal infection and the composition is administered to one or both eyes. In some embodiments of any of the aspects, the subject is one who has received a corneal surgery. In one aspect of any of the embodiments, described herein is a method comprising: performing corneal surgery on one or both eyes of a subject; and then administering a composition as described herein to the one or both eyes. In some embodiments of any of the aspects, the surgery is keratoprosthesis (KPro) implantation, artificial cornea surgery, or cornea replacement surgery.

In some embodiments of any of the aspects, the fungal infection is infectious keratitis and/or endopthalmitis. In some embodiments of any of the aspects, the fungal infection is an infection of *Candida, Candida albicans, Candida parapsilosis, Fusarium,* or *Aspergillus*. In some embodiments of any of the aspects, the composition is administered daily. In some embodiments of any of the aspects, the composition is provided in or on a contact lens, a lower conjunctival fornix device, or a subconjunctival device.

BRIEF DESCRIPTION OF THE DRAWINGS

FIG. 1A) Full-strength Polytrim®: the antibiotic Polytrim® and its components, PMB, TMP, and BAK were tested at full strength. Fungicidal activity was observed in a contact time-dependent manner, except for TMP, which had no effect. Reduction in viable colonies ($<\log_{10}$) was observed within 15 min, with 2 $\log_{10}$ and 3 $\log_{10}$ reductions observed within 60 min and 120 min, respectively. FIG. 1B) Tenth-diluted Polytrim®: fungicidal activity was not observed within the tested contact times for tenth dilutions of Polytrim® and its components. FIG. 1C) Comparator antibiotics: fungicidal activity was not observed within the tested contact times for other commonly used antibiotics (MOX, GAT, CHL, and VAN) without BAK. Viable colonies were counted after 24 hrs of aerobic incubation at 37° C. on Sabouraud dextrose agar. PT=Polytrim®, PMB=polymyxin B sulfate, BAK=benzalkonium chloride, TMP=trimethoprim, MOX=moxifloxacin, GAT=gatifloxacin, CHL=chloramphenicol, VAN=vancomycin. Full strength Polytrim® contains 10,000 u/mL PMB, 40 g/mL BAK, and 1 mg/mL TMP. Concentration of MOX=5 mg/mL, GAT=5 mg/mL, CHL=5 mg/mL, VAN=14 mg/mL. Y-axis displays mean number (±SD) of viable colonies in $\log_{10}$ units from two to three independent experiments performed in technical triplicate. (to be done: p<value versus control at time point by one-way analysis of variance and Tukey multiple comparison test.)

FIG. 2A) Trypan Blue staining: confluent monolayers of HCLE cells were stained with Trypan Blue following 1 min of contact with an antimicrobial agent. Displayed are mean values (±SD) of the % stained area per image. The top four candidates (Polytrim®, BAK, PI, and a novel IL) all had a significantly lower amount of staining (p-value) compared to the control treatment (TX-100), as quantified by universal color thresholding in FIJI™ software (n=3-6 images pertreatment group without overlapping areas). 10× images were obtained under phase contrast microscopy, and results display two to three independent experiments performed in technical duplicate. Fungicidal activity against FIG. 2B) *C. albicans* (ATCC 24433): PI and the novel IL caused a ≥3 $\log_{10}$ reduction in viable colonies within 1 min of contact. CDG was also fungicidal, causing a >log 10 reduction within 1 min, but requiring 5 min to have the same effect as PI and the novel IL. FIG. 2C) *F. solani* (MYA-3636): Polytrim® and PI caused a ≥3 $\log_{10}$ reduction in viable conidia within 1 min of contact. BAK and the novel IL required more time to have the same effect, but still sufficed to cause a 2 $\log_{10}$ reduction within 1 min. FIG. 2D) *A. fumigatus* (MYA-3626): PI and the novel IL caused a 2 $\log_{10}$ and $\log_{10}$ reduction in viable conidia within 1 min, respectively. CDG and Polytrim® had a very moderate effect (<$\log_{10}$ reduction) within 1 min and 15 min of contact, respectively. TX-100=Triton X-100 (1%), PBS=phosphate buffered solution (1×), PT=Polytrim®, BAK=benzalkonium chloride (40 g/mL), PI=povidone iodine (0.5%), #3-IL=ionic liquid (10 mM), CDG=chlorhexidine digluconate (0.05%).

FIGS. 6A-6B depict tissue invasion. Denuded pig corneas were gamma-irradiated and incubated with *C. albicans* (ATCC 24433) to evaluate fungal penetration. Images display cryosections of the FIG. 6A) non-treated and FIG. 6B) gamma-irradiated (25 kGy) tissue taken under epifluorescence microscopy (4×) following calcofluor white staining Infiltration of the *Candida* into the inner stromal layers was observed as faint, vertical lines (marked with arrows) in FIG. 6A). This staining pattern was absent in FIG. 6B). Corneas were aerobically incubated with the *Candida* for 48 hrs at 37° C., and tissue thickness was maintained between the test groups with osmotically balanced medium containing 5% dextran (500 kDa MW).

DETAILED DESCRIPTION

Figure 1A:
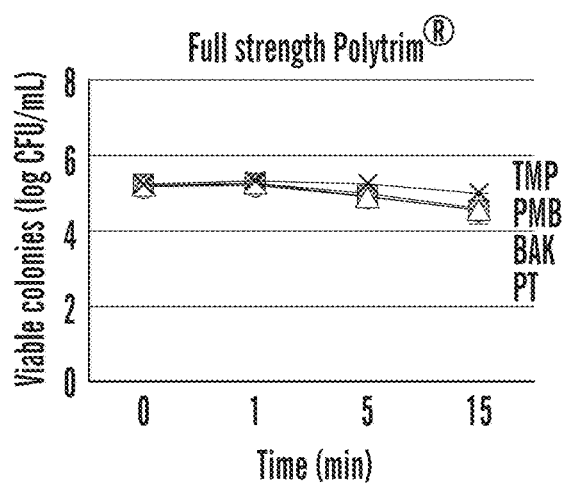
FIGS. 1A-1C demonstrate fungicidal activity against *C. albicans* (ATCC 24433).

As described herein, the ionic liquid choline:undecanoic acid demonstrates surprising antifungal activity, particularly in a corneal environment. It is contemplated herein that the performance of this ionic liquid is surprisingly superior than that of undecanoic acid itself because the ionlic liquid is amphiphilic (as opposed to the hydrophobicity of the undecanoic acid), which provides a) improved ability to remain in suspension and b) superior penetration in biological tissues. Accordingly, in one aspect of any of the embodiments, described herein is a composition comprising comprising at least one ionic liquid comprising a quaternary ammonium cation and an undecanoic acid anion.

The term "ionic liquids (ILs)" as used herein refers to organic salts or mixtures of organic salts which are in liquid state at room temperature. This class of solvents has been shown to be useful in a variety of fields, including in industrial processing, catalysis, pharmaceuticals, and electrochemistry. The ionic liquids contain at least one anionic and at least one cationic component. Ionic liquids can comprise an additional hydrogen bond donor (i.e. any molecule that can provide an —OH or an —NH group), examples include but are not limited to alcohols, fatty acids, and amines. The at least one anionic and at least one cationic component may be present in any molar ratio. Exemplary molar ratios (cation:anion) include but are not limited to 1:1, 1:2, 2:1, 1:3, 3:1, 2:3, 3:2, and ranges between these ratios. For further discussion of ionic liquids, see, e.g., Hough, et ah, "The third evolution of ionic liquids: active pharmaceutical ingredients", New Journal of Chemistry, 31: 1429 (2007) and Xu, et al., "Ionic Liquids: Ion Mobilities, Glass Temperatures, and Fragilities", Journal of Physical Chemistry B, 107(25): 6170-6178 (2003); each of which is incorporated by reference herein in its entirety. In some embodiments of any of the aspects, the ionic liquid or solvent exists as a liquid below 100° C. In some embodiments of any of the aspects, the ionic liquid or solvent exists as a liquid at room temperature.

The cation of an IL described herein can be a cation comprising a quaternary ammonium. A quarternary ammonion is a positively charged polyatomic ion of the structure $NR_4$, each R independently being an alkyl group or an aryl group.

In some embodiments of any of the aspects, the cation has a molar mass equal to or greater than choline, e.g., a molar mass equal to or greater than 104.1708 g/mol. In some embodiments of any of the aspects, the cation has a molar mass greater than choline, e.g., a molar mass equal greater than 104.1708 g/mol.

In some embodiments of any of the aspects, each R group of the quarternary ammoniun independently comprises an alkyl, alkane, alkene, or aryl. In some embodiments of any of the aspects, each R group of the quarternary ammonium independently comprises an alkyl, alkane, or alkene. In some embodiments of any of the aspects, each R group of the quarternary ammoniun independently comprises an alkane or alkene. In some embodiments of any of the aspects, each R group of the quaternernary ammonium independently comprises a carbon chain of no more than 10 carbon atoms in length, e.g., no more than 10, 11, 12, 13, 14, 15, 16, 17, 18, 19, 20, 25, or 30 carbon atoms in length. In some embodiments of any of the aspects, each R group of the quaternernary ammonium independently comprises a carbon chain of no more than 12 carbon atoms in length. In some embodiments of any of the aspects, each R group of the quaternenary ammonium idependently comprises a carbon chain of no more than 15 carbon atoms in length. In some embodiments of any of the aspects, each R group of the quaternernary ammonium independently comprises a carbon chain of no more than 20 carbon atoms in length.

In some embodiments of any of the aspects, each R group of the quaternernary ammonium independently comprises a carbon chain of no more than 10 carbon atoms, e.g., no more than 10, 11, 12, 13, 14, 15, 16, 17, 18, 19, 20, 25, or 30 carbon atoms. In some embodiments of any of the aspects, each R group of the quaternemary ammonium independently comprises a carbon chain of no more than 12 carbon atoms. In some embodiments of any of the aspects, each R group of the quaternernary ammonium independently comprises a carbon chain of no more than 15 carbon atoms. In some embodiments of any of the aspects, each R group of the quaternernary ammonium independently comprises a carbon chain of no more than 20 carbon atoms.

In some embodiments of any of the aspects, each R group of the quaternernary ammonium independently comprises an alkyl group of no more than 10 carbon atoms, e.g., no more than 10, 11, 12, 13, 14, 15, 16, 17, 18, 19, 20, 25, or 30 carbon atoms. In some embodiments of any of the aspects, each R group of the quaternemary ammonium independently comprises an alkyl group of no more than 12 carbon atoms. In some embodiments of any of the aspects, each R group of the quaternernary ammonium independently comprises an alkyl group of no more than 15 carbon atoms. In some embodiments of any of the aspects, each R group of the quaternernary ammonium independently comprises an alkyl group of no more than 20 carbon atoms.

In some embodiments of any of the aspects, each R group of the quaternernary ammonium independently comprises an alkane, alkene, aryl, heteroaryl, alkyl, or heteroalkyl. In some embodiments of any of the aspects, each R group of the quaternernary ammonium independently comprises an unsubstituted alkane, unsubstituted alkene, unsubstituted aryl, unsubstituted heteroaryl, unsubstituted alkyl, or unsubstituted heteroalkyl. In some embodiments of any of the aspects, each R group of the quaternernary ammonium independently an unsubstituted alkane. In some embodiments of any of the aspects, each R group of the quaternernary ammonium independently an unsubstituted alkene. In some embodiments of any of the aspects, each R group of the quaternernary ammonium independently comprises one or more substituent groups.

In some embodiments of any of the aspects, at least one R group of the quaternary ammonium comprises a hydroxy group. In some embodiments of any of the aspects, one R group of the quaternary ammonium comprises a hydroxy group. In some embodiments of any of the aspects, only one R group of the quaternary ammonium comprises a hydroxy group.

Exemplary, non-limiting cations can include choline and any of the cations designated C1-C7 which are defined by structure below.

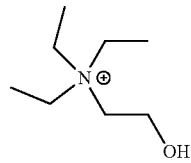

C1

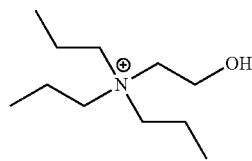

C2

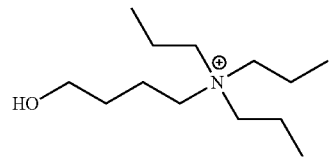

C3

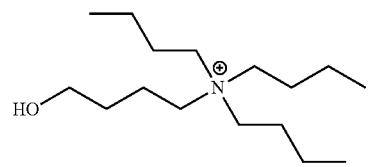

C4

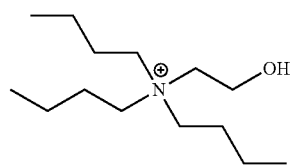

C5

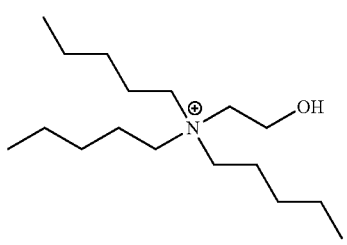

C6

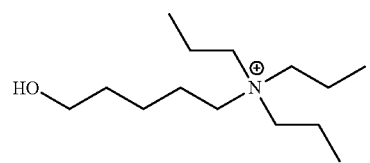

C7

Further non-limiting examples of cations include the following:
1-(hydroxymethyl)-1-methylpyrrolidin-1-ium
1-(2-hydroxyethyl)-1-methylpyrrolidin-1-ium
1-ethyl-1-(3-hydroxypropyl)pyrrolidin-1-ium
1-(3-hydroxypropyl)-1-methylpyrrolidin-1-ium
1-(4-hydroxybutyl)-1-methylpyrrolidin-1-ium
1-ethyl-1-(4-hydroxybutyl)pyrrolidin-1-ium
1-(4-hydroxybutyl)-1-propylpyrrolidin-1-ium
1-(5-hydroxypentyl)-1-propylpyrrolidin-1-ium
1-ethyl-1-(5-hydroxypentyl)pyrrolidin-1-ium
1-(5-hydroxypentyl)-1-methylpyrrolidin-1-ium
1-(hydroxymethyl)-1-methylpiperidin-1-ium
1-(2-hydroxyethyl)-1-methylpiperidin-1-ium
1-ethyl-1-(2-hydroxyethyl)piperidin-1-ium
1-ethyl-1-(3-hydroxypropyl)piperidin-1-ium
1-(3-hydroxypropyl)-1-propylpiperidin-1-ium
1-(3-hydroxypropyl)-1-methylpiperidin-1-ium
1-(4-hydroxybutyl)-1-methylpiperidin-1-ium
1-ethyl-1-(4-hydroxybutyl)piperidin-1-ium
1-(4-hydroxybutyl)-1-propylpiperidin-1-ium
1-butyl-1-(5-hydroxypentyl)piperidin-1-ium
1-(5-hydroxypentyl)-1-propylpiperidin-1-ium
1-ethyl-1-(5-hydroxypentyl)piperidin-1-ium
1-(5-hydroxypentyl)-1-methylpiperidin-1-ium
3-ethyl-1-methyl-1H-imidazol-3-ium
1-methyl-3-propyl-1H-imidazol-3-ium
3-butyl-1-methyl-1H-imidazol-3-ium
1-methyl-3-pentyl-1H-imidazol-3-ium
1,2-dimethyl-3-pentyl-1H-imidazol-3-ium
3-butyl-1,2-dimethyl-1H-imidazol-3-ium
1,2-dimethyl-3-propyl-1H-imidazol-3-ium
3-(hydroxymethyl)-1,2-dimethyl-1H-imidazol-3-ium
3-(2-hydroxyethyl)-1,2-dimethyl-1H-imidazol-3-ium
3-(3-hydroxypropyl)-1,2-dimethyl-1H-imidazol-3-ium
3-(4-hydroxybutyl)-1,2-dimethyl-1H-imidazol-3-ium
3-(5-hydroxypentyl)-1,2-dimethyl-1H-imidazol-3-ium
3-(5-hydroxypentyl)-1-methyl-1H-imidazol-3-ium
3-(4-hydroxybutyl)-1-methyl-1H-imidazol-3-ium
3-(3-hydroxypropyl)-1-methyl-1H-imidazol-3-ium
3-(2-hydroxyethyl)-1-methyl-1H-imidazol-3-ium
3-(hydroxymethyl)-1,2,4,5-tetramethyl-1H-imidazol-3-ium
3-(2-hydroxyethyl)-1,2,4,5-tetramethyl-1H-imidazol-3-ium
3-(3-hydroxypropyl)-1,2,4,5-tetramethyl-1H-imidazol-3-ium
3-(4-hydroxybutyl)-1,2,4,5-tetramethyl-1H-imidazol-3-ium
3-(5-hydroxypentyl)-1,2,4,5-tetramethyl-1H-imidazol-3-ium
1-(5-hydroxypentyl)pyridin-1-ium
1-(4-hydroxybutyl)pyridin-1-ium
1-(3-hydroxypropyl)pyridin-1-ium
1-(2-hydroxyethyl)pyridin-1-ium
1-(hydroxymethyl)pyridin-1-ium
1-hydroxypyridin-1-ium
(hydroxymethyl)trimethylphosphonium
triethyl(hydroxymethyl)phosphonium
triethyl(2-hydroxyethyl)phosphonium
(2-hydroxyethyl)tripropylphosphonium
(3-hydroxypropyl)tripropylphosphonium
tributyl(3-hydroxypropyl)phosphonium
(3-hydroxypropyl)tripentylphosphonium
(4-hydroxybutyl)tripentylphosphonium
(5-hydroxypentyl)tripentylphosphonium In some embodiments of any of the aspects, the cation is choline, C1, C6, and/or C7. In some embodiments of any of the aspects, the cation is C1, C6, and/or C7. In some embodiments of any of the aspects, the cation is choline.

The anion of the ionic liquid described herein is undecanoic acid, also referred to in the art as undecylic acid, is a carboxylic acid with chemical formula $CH_3(CH_2)_9COOH$ and the following structure:

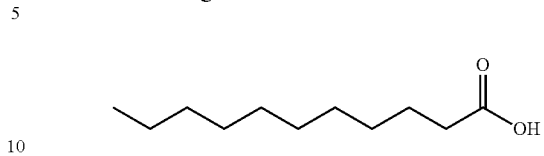

Non-limiting, exemplary combinations of cation and anions are provided in Table 1 below.

TABLE 1

|  | Choline | C1 | C2 | C3 | C4 | C5 | C6 | C7 |
|---|---|---|---|---|---|---|---|---|
| Undecanoic acid | x | x | x | x | x | x | x | x |

In some embodiments of any of the aspects, the IL is at a concentration of at least 0.01% w/v. In some embodiments of any of the aspects, the IL is at a concentration of at least 0.05% w/v. In some embodiments of any of the aspects, the IL is at a concentration of at least 0.1% w/v. In some embodiments of any of the aspects, the IL is at a concentration of at least 0.2% w/v, at least 0.3% w/v, at least 0.4% w/v, at least 0.5% w/v, at least 1% w/v or greater. In some embodiments of any of the aspects, the IL is at a concentration of from about 0.01% w/v to about 1% w/v. In some embodiments of any of the aspects, the IL is at a concentration of from 0.01% w/v to 1% w/v. In some embodiments of any of the aspects, the IL is at a concentration of from about 0.05% w/v to about 0.5% w/v. In some embodiments of any of the aspects, the IL is at a concentration of from 0.05% w/v to 0.5% w/v.

In some embodiments of any of the aspects, the IL is at a concentration of at least 25% w/w. In some embodiments of any of the aspects, the IL is at a concentration of at least 25% w/w in water. In some embodiments of any of the aspects, the IL is at a concentration of at least 25% w/w in saline or a physiologically compatible buffer.

In some embodiments of any of the aspects, the IL is at a concentration of from about 5% w/w to about 75% w/w. In some embodiments of any of the aspects, the IL is at a concentration of from 5% w/w to 75% w/w. In some embodiments of any of the aspects, the IL is at a concentration of from about 5% w/w to about 75% w/w in water, saline or a physiologically compatible buffer. In some embodiments of any of the aspects, the IL is at a concentration of from 5% w/w to 75% w/w in water, saline or a physiologically compatible buffer.

In some embodiments of any of the aspects, the IL is at a concentration of at least about 0.1% w/w. In some embodiments of any of the aspects, the IL is at a concentration of at least 0.1% w/w. In some embodiments of any of the aspects, the IL is at a concentration of from about 10% w/w to about 70% w/w. In some embodiments of any of the aspects, the IL is at a concentration of from 10% w/w to 70% w/w. In some embodiments of any of the aspects, the IL is at a concentration of from about 30% w/w to about 50% w/w. In some embodiments of any of the aspects, the IL is at a concentration of from 30% w/w to 40% w/w. In some embodiments of any of the aspects, the IL is at a concentration of from about 30% w/w to about 50% w/w. In some embodiments of any of the aspects, the IL is at a concentration of from 30% w/w to 40% w/w.

In some embodiments of any of the aspects, the % w/w concentration of the IL is % w/w concentration in water, saline, or a physiologically compatible buffer.

In some embodiments of any of the aspects, the IL is 100% by w/w or w/v.

In some embodiments, the IL is an anhydrous salt, e.g., an ionic liquid not diluted or dissolved in water. In some embodiments, the IL is provided as an aqueous solution.

In some embodiments of any of the aspects, the IL is at a concentration of at least 25% w/w and has a ratio of cation:anion of at least 1:3. In some embodiments of any of the aspects, the IL is at a concentration of at least 25% w/w in water and has a ratio of cation:anion of at least 1:3. In some embodiments of any of the aspects, the IL is at a concentration of at least 25% w/w and has a ratio of cation:anion of 1:3 or 1:4. In some embodiments of any of the aspects, the IL is at a concentration of at least 25% w/w in water and has a ratio of cation:anion of 1:3 or 1:4. In some embodiments of any of the aspects, the IL is a gel, or a shear-thinning Newtonian gel.

In some embodiments of any of the aspects, the IL has a ratio of cation:anion of from about 10:1 to about 1:10. In some embodiments of any of the aspects, the IL has a ratio of cation:anion of from 10:1 to 1:10. In some embodiments of any of the aspects, the IL has a ratio of cation:anion of from about 5:1 to about 1:5. In some embodiments of any of the aspects, the IL has a ratio of cation:anion of from 5:1 to 1:5. In some embodiments of any of the aspects, the IL has a ratio of cation:anion of from about 2:1 to about 1:4. In some embodiments of any of the aspects, the IL has a ratio of cation:anion of from 2:1 to 1:4. In some embodiments of any of the aspects, the IL has a ratio of cation:anion of from about 2:1 to about 1:10. In some embodiments of any of the aspects, the IL has a ratio of cation:anion of from 2:1 to 1:10. In some embodiments of any of the aspects, the IL has a ratio of cation:anion of from about 2:1 to about 1:2. In some embodiments of any of the aspects, the IL has a ratio of cation:anion of from 2:1 to 1:2. In some embodiments of any of the aspects, the IL has a ratio of cation:anion such that there is a greater amount of anion, e.g., a ratio of less than 1:1. In some embodiments of any of the aspects, the IL has a ratio of cation:anion such that there is an excess of anion. In some embodiments of any of the aspects, the IL has a ratio of cation:anion of from about 1:1 to about 1:10. In some embodiments of any of the aspects, the IL has a ratio of cation:anion of from 1:1 to 1:10. In some embodiments of any of the aspects, the IL has a ratio of cation:anion of from about 1:1 to about 1:4. In some embodiments of any of the aspects, the IL has a ratio of cation:anion of from 1:1 to 1:4. In some embodiments of any of the aspects, the IL has a ratio of cation:anion of from about 1:1 to about 1:3. In some embodiments of any of the aspects, the IL has a ratio of cation:anion of from 1:1 to 1:3. In some embodiments of any of the aspects, the IL has a ratio of cation:anion of from about 1:1 to about 1:2. In some embodiments of any of the aspects, the IL has a ratio of cation:anion of from 1:1 to 1:2. In some embodiments of any of the aspects, the IL has a ratio of cation:anion of about 1:1, 1:2, 1:3, or 1:4. In some embodiments of any of the aspects, the IL has a ratio of cation:anion of 1:1, 1:2, 1:3, or 1:4. Without wishing to be constrained by theory, compositions with higher amounts of anion relative to cation display greater hydrophobicity.

In some embodiments of any of the aspects, the IL is at a concentration of at least 20 mM. In some embodiments of any of the aspects, the IL is at a concentration of at least about 20 mM. In some embodiments of any of the aspects, the IL is at a concentration of at least 25 mM. In some embodiments of any of the aspects, the IL is at a concentration of at least about 25 mM. In some embodiments of any of the aspects, the IL is at a concentration of at least 50 mM. In some embodiments of any of the aspects, the IL is at a concentration of at least about 50 mM. In some embodiments of any of the aspects, the IL is at a concentration of at least 100 mM, 500 mM, 1 M, 2 M, 3 M or greater. In some embodiments of any of the aspects, the IL is at a concentration of at least about 100 mM, 500 mM, 1 M, 2 M, 3 M or greater.

In some embodiments of any of the aspects, the IL is at a concentration of from about 50 mM to about 4 M. In some embodiments of any of the aspects, the IL is at a concentration of from 50 mM to 4 M. In some embodiments of any of the aspects, the IL is at a concentration of from about 500 mM to about 4 M. In some embodiments of any of the aspects, the IL is at a concentration of from 500 mM to 4 M. In some embodiments of any of the aspects, the IL is at a concentration of from about 1 M to about 4 M. In some embodiments of any of the aspects, the IL is at a concentration of from 1 M to 4 M. In some embodiments of any of the aspects, the IL is at a concentration of from about 2 M to about 4 M. In some embodiments of any of the aspects, the IL is at a concentration of from 2 M to 4 M.

In some embodiments of any of the aspects, the IL concentration in the composition or formulation is about 0.1 mM to 20 mM. In some embodiments of any of the aspects, the IL concentration in the composition or formulation is about 0.5 mM to 20 mM, 0.5 mM to 18 mM, 0.5 mM to 16 mM, 0.5 mM to 14 mM, 0.5 mM to 12 mM, 0.5 mM to 10 mM, 0.5 mM to 8 mM, 1 mM to 20 mM, 1 mM to 18 mM, 1 mM to 16 mM, 1 mM to 14 mM, 1 mM to 12 mM, 1 mM to 10 mM, 1 mM to 8 mM, 2 mM to 20 mM, 2 mM to 18 mM, 2 mM to 16 mM, 2 mM to 14 mM, 2 mM to 12 mM, 2 mM to 10 mM, 2 mM to 8 mM, 4 mM to 20 mM, 4 mM to 18 mM, 4 mM to 16 mM, 4 mM to 14 mM, 4 mM to 12 mM, 4 mM to 10 mM, 4 mM to 8 mM, 6 mM to 20 mM, 6 mM to 18 mM, 6 mM to 14 mM, 6 mM to 12 mM, 6 mM to 10 mM, 6 mM to 8 mM, 8 mM to 20 mM, 8 mM to 18 mM, 8 mM to 16 mM, 8 mM to 14 mM, 8 mM to 12 mM, 8 mM to 10 mM, 10 mM to 20 mM, 10 mM to 18 mM, 10 mM to 16 mM, 10 mM to 14 mM, 10 mM to 12 mM, 12 mM to 20 mM, 12 mM to 18 mM, 12 mM to 16 mM, 12 mM to 14 mM, 14 mM to 20 mM, 14 mM to 18 mM, 14 mM to 16 mM, 16 mM to 20 mM, 16 mM to 18 mM, or 18 mM to 20 mM. In some embodiments of any of the aspects, the IL concentration in the composition or formulation is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

It is specifically contemplated that a composition described herein can comprise one, two, three, or more of any of the types of components described herein, e.g., active agents, antifungal agents, or ILs. For example, a composition can comprise a mixture, solution, combination, or emulsion of two or more different ionic liquids, and/or a mixture, solution, combination, or emulsion of two or more different non-ionic surfactants, and/or a mixture, solution, combination, or emulsion of two or more different active compounds.

As used herein, "in combination with" refers to two or more substances being present in the same formulation in any molecular or physical arrangement, e.g., in an admixture, in a solution, in a mixture, in a suspension, in a colloid, in an emulsion. The formulation can be a homogeneous or heterogenous mixture. In some embodiments of any of the aspects, the active compound(s) can be comprised by a superstructure, e.g., nanoparticles, liposomes, vectors, cells, scaffolds, or the like, said superstructure is which in solution, mixture, admixture, suspension, etc., with the IL.

In some embodiments of any of the aspects, the composition comprises, consists of, or consists essentially of the one or more ionic liquids comprising comprising a quaternary ammonium cation and a undecanoic acid anion. In some embodiments of any of the aspects, the composition comprises, consists of, or consists essentially of choline: undecanoic acid. In some embodiments of any of the aspects, the composition does not comprise an active agent or ingredient other than the one or more ionic liquids comprising comprising comprising a quaternary ammonium cation and a undecanoic acid anion. In some embodiments of any of the aspects, the composition does not comprise an active agent or ingredient other than choline: undecanoic acid. In some embodiments of any of the aspects, the composition comprises a further active agent or ingredient.

As used herein, an "active compound" or "active agent" is any agent which will exert an effect on a target cell or organism. The terms "compound" and "agent" refer to any entity which is normally not present or not present at the levels being administered and/or provided to a cell, tissue or subject. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. Agents can be known to have a desired activity and/or property, or can be selected from a library of diverse compounds. Non-limiting examples of active compounds contemplated for use in the methods described herein include antifungal agents.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments of any of the aspects, the active compound can be a therapeutic compound or drug, e.g., an agent or compound which is therapeutically effective for the treatment of at least one condition in a subject. Therapeutic compounds are known in the art for a variety of conditions, see, e.g., the database available on the world wide web at drugs.com or the catalog of FDA-approved compounds available on the world wide web at catalog.data.gov/dataset/drugsfda-database; each of which is incorporated by reference herein in its entirety.

In some embodiments of any of the aspects, the active agent can be an antifungal agent, e.g., a further antifungal agent other than the IL describes herein. As used herein, the term "antifungal" refers to any compound known to one of ordinary skill in the art that will inhibit or reduce the growth of, or kill, one or more fungal species. Thus, the ability to inhibit or reduce the growth of, or kill, one or more fungal organisms is referred to herein as "antifungal activity." In some embodiments, an antifungal agent for use in the compositions and methods described herein is "fungistatic," meaning that they stop fungi from reproducing, while not necessarily harming them otherwise. Fungistatic agents limit the growth of fungi by interfering with fungi protein production, DNA replication, or other aspects of fungal cellular metabolism, and typically work together with the immune system to remove fungi from the body. High concentrations of some fungistatic agents are also fungicidal, in some cases, whereas low concentrations of some fungicidal agents are fungistatic. In some embodiments, an antifungal agent (or the effective amount thereof) for use in the compositions and methods described herein is "fungicidal" for the target fungus. That is, the agent kills the target fungal cells and, ideally, is not substantially toxic to mammalian cells. Fungicidal agents include disinfectants, and antiseptics. Many antifungal compounds are relatively small molecules with a molecular weight of less than 2000 atomic mass units. The term "antifungal" includes includes, but is not limited to the antifungals described herein or any salts or variants thereof. The antifugnal used in addition to the potentiator compound in the various embodiments of the compositions and methods described herein will depend on the type of fungal infection.

Major classes of known antifungal agents include, for example, polyenes, imidazoles, triazoles, thiazoles, allylamine, and echinocandins. Accordingly, non-limiting examples of antifungal agents that are suitable for use with the compositions and methods described herein include, without limitation, amphotericin B, candicidin, filipin, hamycin, natamycin, nystatin, rimocidin, bifonazole, butoconazole, clotrimazole, econazole, fenticonzole, isoconazole, ketoconazole, miconazole, omoconazole, oxiconazole, sertaconazole, sulconazole, tioconazole, albaconazole; fluconazole; isavuconazole; itraconazole; posaconazole; ravuconazole; terconazole; voriconazole, abafungin, amorolfin; butenafine; naftifine; terbinafine, anidulafungin; caspofungin; and micafungin.

Antifungal polyenes are macrocvclic polyenes with a heavily hydroxylated region on the ring opposite the conjugated system, rendering them amphiphilic. Polyenes act by binding to sterols, e.g. ergosterol, in the fungal membrane, making the membrane more crystalline. The polyene, amphotericin B (AMB), introduced in the late 1950s, was the first widely utilized antifungal (AF) drug. Due to its strong hydrophobicity, AMB penetrates the fungal membrane and binds to ergosterol leading to membrane damage. Non-limiting examples of polyenes can include amphotericin B; candicidin; filipin; hamycin; natamycin; nystatin; and rimocidin.

Azoles inhibit ergosterol biosynthesis and lead to the accumulation of a toxic methylated sterol that stops cell growth. While azoles tend to be fungistatic due to their poor solubility, under certain conditions and formulations, azoles such as miconazole (MCZ) can be fungicidal. Non-limiting examples of imidazoles can include bifonazole; butoconazole; clotrimazole; econazole; fenticonzole; isoconazole; ketoconazole; miconazole; omoconazole; oxiconazole; sertaconazole; sulconazole; and tioconazole. Non-limiting examples of triazoles can include albaconazole; fluconazole; isavuconazole; itraconazole; posaconazole; ravuconazole; terconazole; and voriconazole. In some embodiments, the antifungal agent can be a thiazole, e.g. abafungin.

Echinocandins inhibit the synthesis of cell wall glucan. Non-limiting examples of echinocandins can include anidulafungin; caspofungin; and micafungin.

Allylamines inhibit squalene epoxidase, which is required for ergosterol biosynthesis. Non-limiting examples of allylamines can include amorolfin; butenafine; naftifine; and terbinafine Further non-limiting examples of antifungal agents can include benzoic acid; ciclopirox; flucytosine; griseofulvin; haloprogin; polygodial; tolnaftate; undecylenic acid; and crystal violet.

In some embodiments of any of the aspects, an antifungal agent can be selected from the group consisting of amphotericin B; natamycin; voriconazole; povidone-iodine; hypochlorous acid; Chlorhexidine digluconate (CDG); vancomycin (VAN); chloramphenicol (CHL); polymyxin B (PMB); trimethoprim (TMP); benzalkonium chloride (BAK); and combinations thereof.

In some embodiments of any of the aspects, the active compound is an antibody or antibody reagent. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

In some embodiments of any of the aspects, a composition as described herein, comprising at least one IL and optionally an active compound can be formulated as an oral, subcutaneous, intravenous, intradermal, ocular, or parenteral formulation. In some embodiments of any of the aspects, the composition described herein can be formulated for ocular administration.

In some embodiments of any of the aspects, described herein is a composition comprising at least one IL as described herein and at least one active compound. In some embodiments of any of the aspects, described herein is a composition consisting essentially of at least one IL as described herein and at least one active compound. In some embodiments of any of the aspects, described herein is a composition consisiting of at least one IL as described herein and at least one active compound. In some embodiments of any of the apsects, the composition comprising at least one IL as described herein and at least one active compound is administered as a monotherapy, e.g., another treatment for the condition is not administered to the subject.

In one aspect of any of the embodiments, described herein is a pharmaceutical composition comprising at least one IL as described herein, and optionally at least one further active agent. In some embodiments, the pharmaceutical composition comprises the at least one IL as described herein. In some embodiments, the pharmaceutical composition consists essentially of the at least one IL as described herein. In some embodiments, the pharmaceutical composition consists of the at least one IL as described herein. In some embodiments, the pharmaceutical composition consists essentially of an aqeuous solution of the at least one IL as described herein. In some embodiments, the pharmaceutical composition consists of an aqeuous solution of the at least one IL as described herein.

In some embodiments, the pharmaceutical composition comprises the at least one IL and the one or more active compounds as described herein. In some embodiments, the pharmaceutical composition consists essentially of the at least one IL and the one or more active compounds as described herein. In some embodiments, the pharmaceutical composition consists of the at least one IL and the one or more active compounds as described herein. In some embodiments, the pharmaceutical composition consists essentially of an aqeuous solution of the at least one IL and the one or more active compounds as described herein. In some embodiments, the pharmaceutical composition consists of an aqeuous solution of the at least one IL and the one or more active compounds as described herein.

The compositions described herein can comprise at least one IL as described herein, e.g., one IL, two ILs, three ILs, or more. In some embodiments of any of the aspects a composition as described herein can comprise at least one IL as described herein and CAGE (Choline And GEranate).

In some embodiments of any of the apsects, the composition comprising at least one ionic liquid as described herein further comprises at least one non-ionic surfactant. As used herein, "non-ionic surfactant" refers to a surfactant which lacks a net ionic charge and does not dissociate to an appreciable extent in aqueous media. The properties of non-ionic surfactants are largely dependent upon the proportions of the hydrophilic and hydrophobic groups in the molecule. Hydrophilic groups include the oxyethylene group ($-OCH_2 CH_2-$) and the hydroxy group. By varying the number of these groups in a hydrophobic molecule, such as a fatty acid, substances are obtained which range from strongly hydrophobic and water insoluble compounds, such as glyceryl monostearate, to strongly hydrophilic and water-soluble compounds, such as the macrogols. Between these two extremes types include those in which the proportions of the hydrophilic and hydrophobic groups are more evenly balanced, such as the macrogol esters and ethers and sorbitan derivatives. Suitable non-ionic surfactants may be found in Martindale, The Extra Pharmacopoeia, 28th Edition, 1982, The Pharmaceutical Press, London, Great Britain, pp. 370 to 379. Non-limiting examples of non-ionic surfactants include polysorbates, a Tween™, block copolymers of ethylene oxide and propylene oxide, glycol and glyceryl esters of fatty acids and their derivatives, polyoxyethylene esters of fatty acids (macrogol esters), polyoxyethylene ethers of fatty acids and their derivatives (macrogol ethers), polyvinyl alcohols, and sorbitan esters, sorbitan monoesters, ethers formed from fatty alcohols and polyethylene glycol, polyoxyethylene-polypropylene glycol, alkyl polyglycoside, Cetomacrogol 1000, cetostearyl alcohol, cetyl alcohol, cocamide DEA, cocamide MEA, decyl glucoside, decyl polyglucose, glycerol monostearate, IGEPAL CA-630, isoceteth-20, lauryl glucoside, maltosides, monolaurin, mycosubtilin, Nonidet P-40, nonoxynol-9, nonoxynols, NP-40, octaethylene glycol monododecyl ether, N-Octyl beta-D-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, sorbitan, sorbitan monolaurate, sorbitan monostearate, sorbitan tristearate, stearyl alcohol, surfactin, Triton X-100, and the like. In some embodiments of any of the aspects, the at least one non-ionic surfactant has a neutral hydrophilic head group.

As used herein, "polysorbate" refers to a surfactant derived from ethoxylated sorbitan (a derivative of sorbitol) esterified with fatty acids. Common brand names for polysorbates include Scattics™, Alkest™, Canarcel™, and Tween™. Exemplary polysorbates include polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate).

In some embodiments of any of the aspects, the at least one non-ionic surfactant (e.g., at least one polysorbate) is present at a concentration of about 0.1% to about 50% w/v. In some embodiments of any of the aspects, the at least one non-ionic surfactant (e.g., at least one polysorbate) is present at a concentration of 0.10% to 50% w/v. In some embodiments of any of the aspects, the at least one non-ionic surfactant (e.g., at least one polysorbate) is present at a concentration of about 1% to about 5% w/v. In some embodiments of any of the aspects, the at least one non-ionic surfactant (e.g., at least one polysorbate) is present at a concentration of 1% to 5% w/v. In some embodiments of any of the aspects, the at least one non-ionic surfactant (e.g., at least one polysorbate) is present at a concentration of about 30% to about 10% w/v. In some embodiments of any of the aspects, the at least one non-ionic surfactant (e.g., at least one polysorbate) is present at a concentration of 3% to 10% w/v. In some embodiments of any of the aspects, the at least one non-ionic surfactant (e.g., at least one polysorbate) is present at a concentration of less than about 5% w/v. In some embodiments of any of the aspects, the at least one non-ionic surfactant (e.g., at least one polysorbate) is present at a concentration of less than 5% w/v.

In some embodiments of any of the aspects, the at least one IL as described herein, and optionally any further active agents, is provided in one or more nanoparticles. In some embodiments of any of the aspects, the composition comprising the at least one IL as described herein, and optionally any further active agents, comprises nanoparticles comprising the active agent, e.g., the nanoparticles are in solution or suspension in a composition comprising at least one IL as described herein.

In some embodiments of any of the aspects, a composition as described herein, e.g., a composition comprising at least one IL and optionally any further active agents, can further comprise a pharmaceutically acceptable carrier. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present disclosure can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

The term "carrier" in the context of a pharmaceutical carrier refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active compound. The term "pharmaceutically acceptable carrier" excludes tissue culture medium.

In some embodiments of any of the aspects described herein, the biological activity of an active agent is improved or stabilized as compared to the activity in the absence of the at least one IL.

The compositions described herein, e.g., those comprising at least one IL comprising comprising a quaternary ammonium cation and a undecanoic acid anion are demonstrated to have surprisingly efficacious antifungal activity coupled with low toxicity. Accordingly, in one aspect of any of the embodiments, described herein is a method of treating or preventing a fungal infection, comprising administering to a subject in need thereof a composition of any of the preceding claims. In some embodiments of any of the aspects, the fungal infection is an ocular fungal infection and the composition is administered to one or both eyes. In some embodiments of any of the aspects, the subject is one who has received a corneal surgery.

Subjects receiving corneal surgery, e.g., keratoprosthesis (KPro) implantation, artificial cornea surgery, or cornea replacement surgery are particularly suspectible to later development of ocular infections. Such subjects frequently receive prophylactic treatments to prevent or slow ocular infections. Accordingly, in some embodiments of any of the aspects, the method further comprises a first step of performing corneal surgery on one or both eyes of the subject. In one aspect of any of the embodiments, described herein is a method comprising performing corneal surgery on one or both eyes of a subject and then administering a composition as described herein, e.g, comprising at least one IL comprising comprising a quaternary ammonium cation and a undecanoic acid anion to the one or both eyes. In some embodiments of any of the aspects, the corneal surgery is keratoprosthesis (KPro) implantation, artificial cornea surgery, or cornea replacement surgery.

The methods described herein can, in some aspects and embodiments, be used to inhibit, delay formation of, treat, and/or prevent or provide prophylactic treatment of fungal infections in animals, including humans.

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to a fungal infection, increase in a fungal infection, or negative effects on the eye from a fungal infection. In some embodiments of any of the aspects, prophylactic treatment is not prevention of all symptoms or signs of a disease.

As used herein, a "fungal infection" refers to an abnormal and/or undesired presence of a fungus in or on a subject. The presence can be abnormal in that the fungus is a noncommensal species, e.g. one not typically found in or on a healthy subject, or it can be abnormal in that the fungus is present at at abnormally high levels, e.g. at least twice the level found in or on a healthy subject (e.g. twice the level, three times the level, four times the level, five times the level, or greater), or it can be abnormal in that the presence of the fungus is causing or contributing to disease or symptoms thereof, e.g. necrosis, disfigurement, delayed wound healing, etc.

In some embodiments, the methods described herein relate to treating a subject having or diagnosed as having a condition with a composition as described herein, e.g, a comprising at least one IL as described herein and and optionally at least one further active agents. Subjects having a condition, e.g., a fungal infection, can be identified by a physician using current methods of diagnosing fungal infections. Diagnosis can be by any suitable means. Diagnosis and monitoring can involve, for example, detecting the level of fungal load in a biological sample (for example, a tissue biopsy, blood test, or urine test), detecting the level of a surrogate marker of the fungal infection in a biological sample, detecting symptoms associated with the infection, or detecting immune cells involved in the immune response typical of fungal infections (for example, detection of antigen specific T cells or antibody production). In some embodiments of any of the aspects, the subject is identified as having a fungal infection by objective determination of the presence of fungal cells in the subject's body by one of skill in the art. Such objective determinations can be performed through the sole or combined use of tissue analyses, blood analyses, urine analyses, and fungal cell cultures, in addition to the monitoring of specific symptoms associated with the fungal infection.

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsu-*

*latum, Coccidioides immitis, Blastomyces dermatitidis, Chlamydia trachomatis, Candida albicans.* Further non-limiting examples of fungal infections include *Candida* spp.; *Cryptococcus* spp.; *Aspergillus* spp.; *Microsporum* spp.; *Trichophyton* spp.; *Epidermophyton* spp.; *Trichosporon* spp.; *Fusarium* spp.; *Tinea versicolor; Tinea barbae; Tinea corporis; Tinea cruris; Tinea manuum; Tinea pedis; Tinea unguium; Tineafaciei; Tinea imbricate; Tinea incognito; Epidermophyton floccosum; Microsporum canis; Microsporum audouinii; Trichophyton interdigitale; Trichophyton mentagrophytes; Trichophyton tonsurans; Trichophyton schoenleini; Trichophyton rubrum; Hortaea werneckii; Piedraia hortae; Malasserziafurfur; Coccidioides immitis; Coccidioides posadasii; Histoplasma capsulatum; Histoplasma duboisii; Lacazia loboi; Paracoccidioides brasiliensis; Blastomyces dermatitidis; Sporothrix schenckii; Penicillium marneffei; Candida albicans; Candida glabrata; Candida tropicalis; Candida lusitaniae; Candida jirovecii; Candida krusei; Candida parapsilosi; Exophiala jeanselmei; Fonsecaea pedrosoi; Fonsecasea compacta; Phialophora verrucosa; Geotrichum candidum; Pseudallescheria boydii; Rhizopus oryzae; Muco indicus; Absidia corymbifera; Synceplasastrum racemosum; Basidiobolus ranarum; Conidiobolus coronatus; Conidiobolus incongruous; Cryptococcus neoformans; Enterocytozoan bieneusi; Encephalitozoon intestinalis*; and *Rhinosporidium seeberi.* In some embodiments of any of the aspects, the fungal infection is infectious keratitis and/or endopthalmitis. In some embodiments of any of the aspects, the fungal infection is an ocular fungal infection. In some embodiments of any of the aspects, the fungal infection is an infection of *Candida, Candida albicans, Candida parapsilosis, Fusarium*, and/or *Aspergillus.* The compositions and methods described herein are contemplated for use in treating infections with these and other fungi.

The compositions and methods described herein can be administered to a subject having or diagnosed as having a condition described herein. In some embodiments, the methods described herein comprise administering an effective amount of compositions described herein, e.g. a compositon comprising at least one IL as described herein and optionally at least one further active agent, to a subject in order to alleviate a symptom of a condition described herein. As used herein, "alleviating a symptom" is ameliorating any marker or symptom associated with a condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or intratumoral administration. Administration can be local or systemic.

In some embodiments of any of the aspects, the administration is transdermal. In some embodiments of any of the aspects, the administration is transdermal, to a mucus membrane (e.g., to a nasal, oral, or vaginal membrane), oral, subcutaneous, intradermal, parenteral, intratumoral, ocular, corneally, or intravenous. In some embodiments of any of the aspects, the administration is provided in or on a contact lens, a lower conjunctival fornix device, or a subconjunctival device.

Formulations for ocular delivery, e.g., ophthalmic delivery can be used in the compositions and methods described herein. Such formulations can generally comprise an admixture of the compositions described herein with an ophthalmically acceptable vehicle. An "ophthalmically acceptable vehicle" is one having physical properties (e.g., pH and/or osmolality) that are physiologically compatible with ophthalmic tissues, e.g., the retina, among others.

In some embodiments of any of the aspects, an ophthalmic composition is formulated as a sterile aqueous solution having an osmolality of from about 200 to about 400 milliosmoles/kilogram water ("mOsm/kg") and a physiologically compatible pH. The osmolality of the solutions can be adjusted, for example, by means of conventional agents, such as inorganic salts (e.g., NaCl), organic salts (e.g., sodium citrate), polyhydric alcohols (e.g., propylene glycol or sorbitol) or combinations thereof.

Ophthalmic formulations can be in the form of liquid, solid or semisolid dosage form. Ophthalmic formulations can comprise, depending on the final dosage form, suitable ophthalmically acceptable excipients. In some embodiments, ophthalmic formulations are formulated to maintain a physiologically tolerable pH range. In certain embodiments, the pH range of an ophthalmic formulation is in the range of from about 5 to about 9. In some embodiments, pH of an ophthalmic formulation is in the range of from about 6 to about 8, or is about 6.5, about 7, or about 7.5. One or more ophthalmically acceptable pH adjusting agents and/or buffering agents can be included in a composition for ophthalmic delivery, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

In some embodiments of any of the aspects, a composition for ophthalmic delivery can be for topical delivery, e.g., in the form of an eye drop. By means of a suitable dispenser, a desired dosage of the active agent can be metered by administration of a known number of drops into the eye, such as by one, two, three, four, or five drops. Additional ocular pharmaceutical compositions and delivery devices are further described, e.g., in U.S. Pat. Nos. 9,993,558 B2; 4,310,543A; 8,668,676 B2, and 4,853,224 A, the contents of each of which are incorporated herein by reference in their entireties.

In some embodiments of any of the aspects, a composition described herein is provided in or on a lower conjunctival fornix device, or a subconjunctival device. Such devices can be implantation devices or diposable devices that can be placed in or on the indicated location where they release the composition, e.g., by diffusion.

Oral administration can comprise providing tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Oral formulations can comprise discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of an ionic liquid as described herein and the at least one active compound, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In some embodiments of any of the aspects, subcutaneous, intradermal or intravenous administration comprises administration via injection, catheter, port, or the like.

In some embodiments of any of the aspects, the composition described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition comprising an ionic liquid as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of an ingredient in a composition as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. While as noted above herein, the compositions as described herein can obviate certain reasons for using a controlled-release formulation, it is contemplated herein that the methods and compositions can be utilized in controlled-release formulations in some embodiments. For example, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active compound, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for blood glucose, among others. The dosage can be determined by a physician and adjusted, as necessary, to suit observed effects of the treatment.

In some embodiments of any of the apsects, the composition as described herein, e.g., a composition comprising at least one IL as described herein is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy, either in the composition described herein, e.g., a composition comprising at least one IL as described herein, or as a separate formulation. For example, non-limiting examples of a second agent and/or treatment for the subject described herein include further antifungal agents as described elsewhere herein as well as antibiotic agents to prevent bacterial infections.

As used herein, "antibiotic" refers to any chemical or biological agent with therapeutic usefulness in the inhibition of bacterial cell growth or in killing bacteria, e.g, those that are bactericidal or bacteriostatic. Categories of antibiotics can include, but are not limited to those that target the bacterial cell wall (e.g., penicillins, cephalosporins), those that target the bacterial cell membrane (e.g., polymyxins), those that target bacterial enzymes (e.g., rifamycins, lipiarmycins, quinolones, sulfonamides), protein synthesis inhibitors (e.g., macrolides, lincosamides, and tetracyclines), aminoglycosides, cyclic lipopeptides, glycyclines, oxazolidinones, beta-lactams, and lipiarmycins. Exemplary, non-limiting antibiotics include penicillin, methicilling, nafcillin, oxacillin, cloxacillin, dicloxacillin, flucloxacillin, ampicillin, amoxicillin, pivampicillin, hetacillin, bacampicillin, metampicillin, talamipicillin, epicillin, cabenicillin, ticaricillin, temocillin, mezlocillin, piperacillin, azolocillin, clavulanic acid, sulbactam, tazobactam, cafadroxil, cephalexin, cefalotin, cefapirin, cefazolin, cefradine, cefaclor, cefonicid, cefprozil, cefuroxime, loracarbef, cefmetazole, cefotetan, cefoxitin, cefotiam, cefdinir, cefixime, cefotaxime, cefovecin, cefpodoxime, ceftibuten, ceftiofur, ceftizoxime, ceftriaxone, cefoperazone, ceftazimdime, latamoxef, cefepime, cefiderocol, cefpriome, rifampicin, rifabutin, rifapentine, rifamixin, fidaxomicin, ciproflaxicin, moxifloxacin, levofloxacine, sulfafurzole, azithromycin, clarithromycin, erythromycin, fidaxomicin, spiramycin, telihtromycin, lincomycin, clindamycin, pirlimycin, tetracycline, eravacycline, sarecycline, omadacycline, doxycycline, kanamycin, tobramycin, gentamicin, neomycin, streptomycin, vancomycin, tigecycline, linezolid, posizolid, tedizolid, radezolid, cycloserine, contezolid, and daptomycin. In some embodiments of any of the aspects, the antibiotic is one or more of tobramycin, trimethroprim, ciprofloxacin, gatifloxacin, moxifloxacin, fluoroguinolones, cefazolin, and vancomycin. One of skill in the art can readily identify an antibiotic agent of use e.g. see Antibiotics in Laboratory Medicine, Victor Lorian (ed.) Wolters Kluwer; and Antibotics Manual, David Schlossberg and Rafik Samuel, John Wiley and Sons (2017); each of which is incorporated by reference herein in its entirety.

In certain embodiments, an effective dose of a composition described herein, e.g, a composition comprising at least one IL as described herein, can be administered to a patient once. In certain embodiments, an effective dose a composition described herein, e.g., a composition comprising at least one IL as described herein, can be administered to a patient repeatedly. In certain embodiments, an effective dose a composition described herein, e.g, a composition comprising at least one IL as described herein, can be administered to a patient daily. For systemic administration, subjects can be administered a therapeutic amount of a composition described herein, e.g, a composition comprising at least one IL as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. In some embodiments of any of the aspects, the at least one IL is present at a dose of from 1.0-20.0 mg/kg. In some embodiments of any of the aspects, the at least one IL is present at a dose of from about 1.0-about 20.0 mg/kg.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active compound. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition described herein, e.g, a composition comprising at least one IL as described herein, can be administered over a period of time, such as over a 5 minute, 10 minute, 15 minute, 20 minute, or 25 minute period.

The dosage ranges for the administration of the compositions described herein, according to the methods described herein depend upon, for example, the form of the active compound, its potency, and the extent to which symptoms, markers, or indicators of a condition described herein are desired to be reduced, for example the percentage reduction desired for symptoms or markers. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition described in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of diabetes or cancer. When using an experimental animal model, efficacy of treatment is evidenced when a statistically significant change in a marker is observed.

In vitro and animal model assays are provided herein which allow the assessment of a given dose of a composition described herein, e.g, a composition comprising at least one IL as described herein. By way of non-limiting example, the effects of a dose of a composition comprising at least one IL as described can be assessed by using the models described in the Examples herein, e.g, fungal growth in vitro and/or in a corneal model.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

A carboxylic acid is a carbonyl-bearing functional group having a formula RCOOH where R is aliphatic, heteroaliphatic, alkyl, or heteroalkyl.

As used herein, the term "alkyl" means a straight or branched, saturated aliphatic radical having a chain of carbon atoms. The term "alkyl" includes cycloalkyl or cyclic alkyl. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., $(C_6$-$C_{10})$aryl$(C_0$-$C_3)$alkyl includes phenyl, benzyl, phenethyl, 1-phenylethyl 3-phenylpropyl, and the like. Backbone of the alkyl can be optionally inserted with one or more heteroatoms, such as N, O, or S. Examples of alkyl radicals include, but are not limited to, methyl, ethyl, propyl, isopropyl, n-butyl, tert-butyl, neopentyl, n-hexyl, and n-octyl radicals.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-Cyalkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine. A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. Examples of cyclyl groups include, without limitation, cyclopropyl, cyclobutyl, cyclopentyl, cyclopentenyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies. As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

As used herein, the term "substituted" refers to independent replacement of one or more of the hydrogen atoms on the substituted moiety with substituents independently selected from, but not limited to, alkyl, alkenyl, heterocycloalkyl, alkoxy, aryloxy, hydroxy, amino, amido, alkylamino, arylamino, cyano, halo, mercapto, nitro, carbonyl, acyl, aryl and heteroaryl groups.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —$NH_2$. The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —$NH(C_1$-$C_{10}alkyl)$, —$N(C_1$-$C_{10}alkyl)_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —$N(aryl)_2$. The term "heteroarylamino" means a nitrogen moiety having at least one heteroaryl radical attached to the nitrogen. For example —NHheteroaryl, and —$N(heteroaryl)_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —$OCH_2CH_2OCH_3$, and the like. The term "alkoxycarbonyl" means —C(O)O-(alkyl), such as —C(=O)$OCH_3$, —C(=O)$OCH_2CH_3$, and the like. The term "alkoxyalkyl" means -(alkyl)-O-(alkyl), such as —$CH_2OCH_3$, —$CH_2OCH_2CH_3$, and the like. The term "aryloxy" means —O-(aryl), such as —O-phenyl, —O-pyridinyl, and the like. The term "arylalkyl" means -(alkyl)-(aryl), such as benzyl (i.e., —$CH_2$phenyl), —$CH_2$-pyrindinyl, and the like. The term "arylalkyloxy" means —O-(alkyl)-(aryl), such as —O-benzyl, —O—$CH_2$-pyridinyl, and the like. The term "cycloalkyloxy" means —O-(cycloalkyl), such as —O-cyclohexyl, and the like. The term "cycloalkylalkyloxy" means —O-(alkyl)-(cycloalkyl, such as —$OCH_2$cyclohexyl, and the like. The term "aminoalkoxy" means —O-(alkyl)-$NH_2$, such as —$OCH_2NH_2$, —$OCH_2CH_2NH_2$, and the like. The term "mono- or di-alkylamino" means —NH(alkyl) or —N(alkyl)(alkyl), respectively, such as —$NHCH_3$, —N($CH_3$)$_2$, and the like. The term "mono- or di-alkylaminoalkoxy" means —O-(alkyl)-NH(alkyl) or —O-(alkyl)-N(alkyl)(alkyl), respectively, such as —$OCH_2NHCH_3$, —$OCH_2CH_2N(CH_3)_2$, and the like. The term "arylamino" means —NH(aryl), such as —NH-phenyl, —NH-pyridinyl, and the like. The term "arylalkylamino" means —NH-(alkyl)-(aryl), such as —NH-benzyl, —$NHCH_2$-pyridinyl, and the like. The term "alkylamino" means —NH(alkyl), such as —$NHCH_3$, —$NHCH_2CH_3$, and the like. The term "cycloalkylamino" means —NH-(cycloalkyl), such as —NH-cyclohexyl, and the like. The term "cycloalkylalkylamino"-NH-(alkyl)-(cycloalkyl), such as —$NHCH_2$-cyclohexyl, and the like.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH3) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The term "racemic mixture", "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); or (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(−)}$ (where the sum of $F_{(+)}$ and $F_{(−)}$=1). The enantiomeric excess is defined as *$F_{(+)}$-$F_{(−)}$* and the percent enantiomeric excess by 100×*$F_{(+)}$-$F_{(−)}$*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer", "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer", "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity", also called the enantiomeric ratio indicated by the symbol "E", refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions described herein. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. See U.S. patent application 20040161738 publishedAug. 19, 2004; which is incorporated by reference herein in its entirety. These features combined with the low antigenicity to humans indicate great therapeutic potential.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., cDNA. Suitable RNA can include, e.g., mRNA.

As used herein, "inhibitory nucleic acid" refers to a nucleic acid molecule which can inhibit the expression of a target, e.g., double-stranded RNAs (dsRNAs), inhibitory RNAs (iRNAs), and the like.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art. In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a condition or disease described herein. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the at least one IL as described herein in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "effective amount" means an amount of a composition sufficient to provide at least some amelioration of the symptoms associated with the condition. In one embodiment, the "effective amount" means an amount of a composition would decrease the markers or symptoms of the condition in a subject having the condition.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean+1%.

As used herein, the term "comprising" or "comprises" is used in reference to methods and compositions, and respective component(s) thereof, that are essential to the invention, yet open to the inclusion of unspecified elements, whether essential or not. As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A composition comprising at least one ionic liquid comprising a quaternary ammonium cation and an undecanoic acid anion.
2. The composition of paragraph 1, wherein the cation has a molar mass equal to or greater than choline.
3. The composition of any of the preceding paragraphs, wherein the quaternary ammonium has the structure of $NR_4^+$ and at least one R group comprises a hydroxy group.
4. The composition of any of the preceding paragraphs, wherein the quaternary ammonium has the structure of $NR_4^+$ and only one R group comprises a hydroxy group.
5. The composition of any of the preceding paragraphs, wherein the cation is choline, C1, C6, or C7.
6. The composition of any of the preceding paragraphs, wherein the ionic liquid is at a concentration of at least 0.10% w/v.
7. The composition of any of the preceding paragraphs, wherein the ionic liquid is at a concentration of from about 10 to about 70% w/v.
8. The composition of any of the preceding paragraphs, wherein the ionic liquid is at a concentration of from about 30 to about 50% w/v.
9. The composition of any of the preceding paragraphs, wherein the ionic liquid is at a concentration of from about 30 to about 40% w/v.
10. The composition of any of the preceding paragraphs, wherein the ionic liquid comprises a ratio of cation to anion of from about 2:1 to about 1:10.
11. The composition of any of the preceding paragraphs, wherein the ionic liquid comprises a ratio of cation to anion of from about 1:1 to about 1:4.
12. The composition of any of the preceding paragraphs, wherein the ionic liquid comprises a ratio of cation to anion of about 1:1.
13. The composition of any of the preceding paragraphs, wherein the ionic liquid has a cation:anion ratio of 1:1.
14. The composition of any of the preceding paragraphs, wherein the composition does not comprise an active agent other than the at least one ionic liquid.
15. The composition of any of the preceding paragraphs, wherein the composition further comprises an active compound other than the at least one ionic liquid.
16. The composition of any of the preceding paragraphs, wherein the composition is formulated for administration transdermally, to a mucus membrane, orally, ocularly, subcutaneously, intradermally, parenterally, intratumorally, or intravenously.
17. The composition of paragraph 16, wherein the composition is formulated for ocular administration.
18. The composition of any of the preceding paragraphs, further comprising one or more additional antifungal agents.
19. The composition of paragraph 18, wherein the one or more additional antifungal agents are selected from the group consisting of:
Amphotericin B; natamycin; voriconazole; povidone-iodine; hypochlorous acid; Chlorhexidine digluconate (CDG); vancomycin (VAN); chloramphenicol (CHL); polymyxin B (PMB); trimethoprim (TMP); benzalkonium chloride (BAK); and combinations thereof.
20. A method of treating or preventing a fungal infection, comprising administering to a subject in need thereof a composition of any of the preceding paragraphs.
21. The method of any of the preceding paragraphs, wherein the administration is transdermal, to a mucus membrane, oral, subcutaneous, intradermal, parenteral, intratumoral, ocular, or intravenous.
22. The method of paragraph 21, wherein the fungal infection is an ocular fungal infection and the composition is administered to one or both eyes.
23. The method of any of the preceding paragraphs, wherein the subject is one who has received a corneal surgery.
24. A method comprising:
   a) performing corneal surgery on one or both eyes of a subject; and
   b) administering a composition of any of paragraphs 1-19 to the one or both eyes.
25. The method of any of the preceding paragraphs, wherein the surgery is artificial cornea surgery.
26. The method of any of the preceding paragraphs, wherein the fungal infection is infectious keratitis and/or endopthalmitis.
27. The method of any of the preceding paragraphs, wherein the fungal infection is an infection of *Candida, Candida albicans, Candida parapsilosis, Fusarium*, or *Aspergillus*.
28. The method of any of the preceding paragraphs, wherein the composition is administered daily.
29. The method of any of the preceding paragraphs, wherein the composition is provided in or on a contact lens, a lower conjunctival fornix device, or a subconjunctival device.

The technology described herein is further illustrated by the following examples which in no way should be construed as being further limiting.

EXAMPLES

Example 1

There is an unmet need for prophylaxis against fungal infections following keratoprosthesis (KPro) implantation. Described herein is the evaluation of the antifungal properties of topical antibiotics preparation that are already being used successfully to prevent bacterial endophthalmitis, as well as some promising antiseptics.

Several commonly used antibiotics were tested in vitro against *Candida albicans* (ATCC 24433), *Fusarium solani* (ATCC MYA-3636), and *Aspergillus fumigatus* (ATCC MYA-3626). Time kill activity and minimum inhibitory concentrations (MIC) were determined. Also the antiseptics benzalkonium chloride (BAK), povidone-iodine (PI), and ionic liquids (ILs) consisting of a 1:1 mixture of choline and undecanoic acid, were tested. Toxicity was assayed in vitro on cultures of human corneal epithelial cells, subjected to Trypan Blue staining. Adhesion and tissue invasion experiments were also carried out, with or without γ-irradiation, and by analysis with fluorescent microscopy.

Polymyxin B (PMB)/trimethoprim (TMP)/BAK (Polytrim®), PMB alone, gatifloxacin (GAT) with BAK (Zymaxid®), and same-concentration BAK alone, exhibited moderate antifungal activity in vitro. A log unit dilution markedly reduced efficacy. Moxifloxacin (MOX) or GAT without BAK, as well as TMP, vancomycin (VAN), and chloramphenicol (CHL), had no effect. 1% PI had good efficacy/toxicity ratio and IL performed even better. Polytrim® reduced adhesion of C. albicans to Kontur™ contact lenses, which are used for Gamma-irradiated corneas, without additional agents, showed enhanced resistance to fungal invasion.

Of the antibiotic preparations already in use for bacterial prophylaxis after KPro surgery, Polytrim® has broad spectrum antibacterial effect and is very inexpensive. Its fungicidal effect is caused by both PMB and BAK. Polytrim®'s effect on fungi is weak but may be sufficient for prophylaxis. PI, used for decades in ophthalmology, as a 1% solution appears to be promising as a long-term antifungal. Hypochlorous acid has previously been shown to have promise. The here synthesized choline-undecanoate IL is effective and virtually non-toxic.

Introduction

One of the most serious and feared complications following artificial cornea surgery (KPro) is still infectious keratitis and/or endophthalmitis. The introduction of bandage soft contact lenses and daily, low-dose prophylactic antibiotic drops postoperatively for life have sharply reduced the incidence of bacterial endophthalmitis, yet fungal infections remain as an issue to be addressed.[1-5] In the Northern hemisphere, the causative organisms have most commonly been Candida albicans and Candida parapsilosis. In the hot and humid climates of under-resourced countries, fungal infections pose a much more significant problem. There the causative organisms have most commonly been filamentous fungi such as Fusarium and Aspergillus.[6,7] In a recent study on KPro use in India, it was noted that fungal etiology of postoperative endophthalmitis occurred in almost equal numbers as those with bacterial endophthalmitis.[8]

Thus, there is clearly an unmet need for an effective, inexpensive, simply applied antifungal prophylactic treatment. One way to fill this need would be to adopt existing, well-established antifungals with proven efficacy such as amphotericin B, natamycin, voriconazole, or others. These medications would be expected to be very efficient as prophylaxis, but are challenged by the need for compounding, chemical instability with resulting need for frequent replacement, or high cost, in addition to adding to the burden of self-medication. Development of resistance may also be a long-term problem.

Another possible route, already taken by several surgeons, might be to use an antiseptic eye drop like povidone-iodine (PI), which has broad-spectrum activity and has for decades been utilized in preparation for ophthalmic surgery.[9-12] It has also been suggested for prophylactic antimicrobial use after KPro implantation,[12,13] and (anecdotally) implemented by other KPro surgeons. However, ocular inflammation from long-term use has occurred. More recently, 0.01% hypochlorous acid (Avenova®; Novabay Pharmaceuticals; Emeryville, Calif.) has been evaluated for daily antifungal prophylaxis. It was found to have rapid fungicidal and sporicidal activity within one minute of exposure time, with broad-spectrum activity against Candida, Aspergillus, and Fusarium in vitro.[2] This agent is well tolerated and is FDA-approved for the treatment of blepharitis. However, the manufacturing process is not a simple one, and thus, may introduce concerns of cost and instability. Chlorhexidine digluconate (CDG) and newer type of antimicrobial, ionic liquids (ILs), based on a combination of choline and a medium-chain fatty acid, undecanoic acid,[4-19] are also promising candidate anti-fungals for potential prophylactic use.

A third possibility would be to examine antibiotic formulations already in use for antibacterial prophylaxis and examine them for possible antifungal activity, which would simplify the medication burden for the patient and reduce cost. An indication that this route might be fruitful comes from a recent publication by Behlau et al, 2014 on the incidence rate of endophthalmitis after Boston KPro (B-KPro). In a cohort of non-autoimmune patients, treated with one drop of Polytrim® (polymyxin B (PMB)/trimethoprim (TMP)/benzalkonium chloride (BAK)) per day as antibacterial prophylaxis for four years, no infection (bacterial or fungal) was observed, whereas when other antibiotics (e.g. fluoroquinolones, FQ's) were exclusively used, several fungal infections occurred.[20] (One-tailed Fisher exact test: p=0.057; two-tailed: p=0.101; H. Lee, 2018)

For the B-KPro, the leading choices worldwide in the past for prophylactic antibiotic drops against bacteria have been Polytrim®, FQ's, vancomycin (VAN), and chloramphenicol (CHL), with or without the addition of BAK. These drugs as well as the above-mentioned antiseptic compounds are tested herein for efficacy and toxicity in vitro against C. albicans, F. solani, and A. fumigatus, the most common causative agents of KPro-related fungal infections.[3]

Materials and Methods

Fungal Culture.

American Type Culture Collection (ATCC) strains of C. albicans (ATCC 24433), F. solani (ATCC MYA3636) and A. fumigatus (ATCC MYA3626) were purchased and used for testing. Yeasts were aerobically grown on Sabouraud dextrose agar (Difco; Detroit, Mich.) at 37° C. for 24 h. Filamentous fungi were aerobically grown on potato dextrose agar (Becton Vickinson; Cockeysville, Md.) at 25-35° C. for 5 days.

Antimicrobial Agents

Polytrim® (Allergan; Irvine, Calif.) eye drops, PI solution (Ricca Chemical; Arlington, Tex.), and CDG (Sigma Aldrich; St Louis, Mo.) were purchased. PMB, TMP, BAK, GAT, MOX, VAN, and CHL (Sigma-Aldrich; St Louis, Mo.) were prepared at the concentration of their commercially marketed eye drop preparations, and tested for quality control of antibacterial activity according to the Clinical Laboratory Standards Institutes (CLSI) methods (M100).[21] Choline-based ionic liquids containing undecanoate in a 1:1 ratio, were synthesized as described below, and a 100 mM stock solution in Milli Q water was prepared. Test solutions were diluted in Roswell Park Memorial Institute-1640 broth (RPMI; buffered with 3-(N-Morpholino)propanesulfonic acid, or MOPS, at pH 7.0; Mediatech; Manassas, Va.) for the time kill experiments. Tonicities of the best solutions were determined.

In Vitro Time Kill Tests. Microtiter time kill tests were carried out in vitro according to the published CLSI methods (M27-A2).[22]

i) Yeast: The antibiotic solutions, at either full or $\frac{1}{10}$ strength, and antiseptics were inoculated with $1 \times 10^5$-$2 \times 10^6$ CFU/mL of *C. albicans* in RPMI broth (buffered with MOPS at pH 7.0; Mediatech; Manassas, Va.) for 0-15 min. The inoculum was prepared by adjustment of the optical density at 600 nm ($OD_{600}$) to 1.0 (corresponding to approximately $1×10^6$ CFU/mL), and dilution by 1:10 in the final solution. To confirm the starting inoculum size, yeasts were plated on? and colonies counted after growth for 24 hrs at 37° C. The test solutions were neutralized at each time point by ten-fold dilution in Dey-Engley neutralizing broth (Sigma-Aldrich; St Louis, Mo.), and serially track diluted (PMID: 9343684) on Sabouraud dextrose agar (six serial 1:10 dilutions, 0.01 mL each) in technical triplicate. Colonies were counted and recorded following aerobic incubation for 24 hrs at 37° C.

ii) Filamentous fungi: The antibiotic solutions, at either full or 1/10 strength, and antiseptics were inoculated with approximately $2×10^5$-$2×10^6$ conidia/mL of *F. solani* or *A. fumigatus* in RPMI broth (buffered with MOPS at pH 7.0; Mediatech; Manassas, Va.) for 0-15 min. Conidia were collected by flooding the agar plates with 10 mL of sterile 1×PBS and 0.1% Tween® 20 (Sigma Aldrich; St Louis, Mo.). The solution was transferred to a sterile conical tube, and particles were allowed to settle for 10 min. The resulting supernatant was transferred to a new sterile conical tube and centrifuged at 3,000×g for 5 min. The supernatant was discarded, the remaining pellet was re-suspended in RPMI broth (buffered with MOPS at pH 7.0), and the $OD_{600}$ was adjusted to 1.0. In the final test solutions, at each time point the inoculum was diluted 1:10 and neutralized in Dey-Engley neutralizing broth (Sigma-Aldrich; St Louis, Mo.). Neutralized cultures were then serially diluted and plated on Sabouraud dextrose agar (two serial 1:10 dilutions, 0.1 mL each) in technical duplicate. Viable conidia were counted and recorded following aerobic incubation for 48 hrs (or as soon as growth was visible) at 25-35° C.

Choline undecanoate (1:1). Choline bicarbonate (80% in water, Sigma Aldrich) was combined, with vigorous stirring, with undecanoic acid (98%, Sigma Aldrich) in a 1:1 molar ratio at 40° C. The mixture was left stirring overnight, then dried in a rotary evaporator at 10 mbar and 60° C. for 2 hrs, before being placed in a vacuum oven at 60° C. for 72 hrs. The resulting product was a malleable amber semisolid, and the chemical identity was confirmed by Nuclear Magnetic Resonance Spectroscopy, with peaks identified as follows: $^1H$ NMR (600 MHz, d-DMSO) 0.84 (dt, 3H, OOCCH$_2$CH$_2$CH$_2$CH$_2$CH$_2$CH$_2$CH$_2$CH$_2$CH$_2$CH$_3$); 1.22-1.36 (m, 16H, OOCCH$_2$CH$_2$(CH$_2$)$_8$CH$_3$); 1.72 (h, 2H, OOCCH$_2$CH$_2$(CH$_2$)$_8$CH$_3$); 3.31 (q, 2H, OOCCH$_2$CH$_2$(CH$_2$)$_8$CH$_3$); 3.08 (s, 9H, NCH$_3$); 3.37 (h, 2H, NCH$_2$CH$_2$OH); 3.82 (h, 2H, NCH$_2$CH$_2$OH).

In Vitro Toxicity Tests. Trypan Blue assays for toxicity of various antimicrobial agents were conducted using human corneal cells. Telomerase-immortalized human corneal-limbal epithelial cells (HCLE) were thawed at 37° C. and quickly transferred to a sterile T75 cell culture flask. Cells were grown in keratinocyte serum-free medium (KSFM; Gibco™; Thermofisher Scientific; Waltham, Mass.) supplemented with bovine pituitary extract (25 μg/mL), epidermal growth factor (0.2 ng/mL), calcium chloride (0.4 mM CaCl$_2$☐2H$_2$O; Sigma-Aldrich; St Louis, Mo.), and 1× penicillin/streptomycin, at 37° C. with 5% $CO_2$. Once cells were confluent, they were passaged following trypsinization in 12- or 24-well plates. After incubation with Trypsin-EDTA (0.05%, Gibco™; Thermofisher Scientific; Waltham, Mass.) for 5-10 min at 37° C. with 5% $CO_2$, the reaction was stopped with an equivalent volume of neutralizing medium (Dulbecco's Modified Eagle Medium/Nutrient Mixture F-12, DMEM/F-12, with HEPES and 10% newborn calf serum), centrifuged at 5,000×g for 5 min, and re-suspended in supplemented KSFM. Experiments were performed using cells from passages 31 to 36. Once cells reached confluency, they were gently washed twice with DMEM/F-12 (Gibco™; Thermofisher Scientific; Waltham, Mass.) and incubated with an antimicrobial agent for 1 min (n=2 wells per group). Controls included 1×PBS (diluent) and 1% TX-100 (cell permeabilizer). After exposure to various agents, the cells were washed three times with DMEM/F-12, incubated with 0.2% Trypan Blue for 5 min, and washed again three times with DMEM/F-12. The remaining media was aspirated and replaced with 1×PBS for imaging. Macro-images of the culture plate were taken with a smartphone camera (iPhone 7; Apple Inc.; Cupertino, Calif.), and 10× images were taken with an inverted microscope (Eclipse TS100; Nikon; Tokyo, Japan) attached to a digital camera (SPOT Insight Fire Wire; Diagnostic Instruments Inc.; Sterling Heights, Mich.). 3-6 images/well were obtained in clockwise direction from areas immediately adjacent to the center of the well, and without overlapping areas. Images were quantified in ImageJ Fiji software to determine the amount of cell uptake of Trypan Blue. Macros were created from the Color Threshoulder plugin (G. Landini) to batch process the images after color matching in Photoshop to reference images per treatment group. % Area of Trypan Blue staining per image was calculated as follows: (area of blue/area of all)×100%.

In Vitro Adhesion Tests. Polytrim® was diluted 1/10 and 1/100 in sterile PBS, and combined with *C. albicans* ($OD_{600}$ adjusted to 1.5) for 90 min at 37° C. Following incubation, the cells were washed three times (centrifugation at 3000×g for 5 min) and resuspended in PBS to remove trace amounts of the antibiotics. Kontur™ soft contact lenses (Kontur Kontact Lens; Hercules, Calif.) were placed in a sterile 24-well tissue culture plate (Corning; Corning, N.Y.) containing 1 mL of the pre-treated fungal cells. (Positive controls contained non-treated fungal cells, and negative controls contained only sterile PBS.) The plates were aerobically incubated for 24 hrs at 37° C. with gentle movement (machine, speed), and carefully washed three times with 1 mL PBS. To remove fungal cells potentially adhering to the soft contact lenses, the tissue culture plate was sonicated in a sonifier bath (Branson2400; Branson Ultrasonics; Danbury, Conn.) for 1 min at maximum strength, and manually agitated by nudging with a sterile micropipettor tip for an additional 10 sec. The remaining solution was serially diluted, plated onto Sabouraud dextrose agar (0.1 mL) in technical triplicate, and viable colonies were counted and recorded following aerobic incubation for 24 hrs at 37° C.

Ex Vivo Tissue Invasion Tests. Porcine globes were purchased (VisionTech; Mesquite, Tex.), and grossly examined to exclude eyes with detectable corneal surface defects or stromal opacities. Corneoscleral rims were dissected using a surgical blade and fine scissors, gently denuded with a surgical blade and Weck-Cel® sponge (XOMED Surgical Products; Jacksonville, Fla.), and immersed in corneal storage medium with DMEM/F-12 (Gibco™; Thermofisher Scientific; Waltham, Mass.) and 5% dextran (500 kDa; Thermo Fisher Scientific; Waltham, Mass.). All eyes were stored at −80° C. before experiments. For treatment groups, the corneoscleral rims were gamma-irradiated at 25 kGy according to standard sterilization procedure. The treated and non-treated corneoscleral rims were immersed together in a solution with *C. albicans* (corneal storage medium with an $OD_{600}$ of 2.0), and incubated for 48 hrs at 37° C. with shaking (speed) on a (model). Smaller-size corneal buttons were obtained by dissection with a trephine (7 mm; Acuderm Inc.; Ft. Lauderdale, Fla.), and subsequently washed in 1 mL of sterile 1×PBS. The buttons were embedded in Tissue-TEK OCT compound (Sakura Finetek; Zoeterwoude, The Netherlands), flash frozen on dry ice, and cut into 10 uM thick sections (machine). The sections were fixed in 4% paraformaldehyde, stained with calcofluor white (Sigma-Aldrich; St Louis, Mo.), and examined under an epifluorescent microscope (Leica DM5500B; Leica Microsystems; Buffalo Grove, Ill.). Images (4×) were captured with a (camera type), and saved.

Results

To investigate the fungicidal activity of various antibiotics and antimicrobials, the reduction in fungal load after short contact times (0-15 min, FIGS. 2-3), to account for the effect of rapid dilution by the tear film, as occurs in patients after topical instillation, was measured.[23] The detection limit for time kill tests was approximately 100 CFU/mL for *C. albicans*, and 1 CFU/mL for *F. solani* and *A. fumigatus* (corresponding to a ≥3 log difference from the starting inoculum). 20-300 cells were considered a reliable counting range per dilution, and values were averaged when more than one dilution in the same plate were within this range.

Polytrim® Exhibits Some Fungicidal Activity, Attributable to Both PMB and BAK.

Figure 1B:
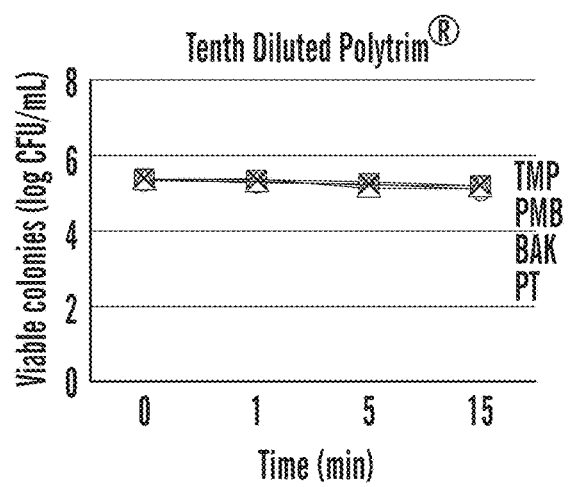

Overall, depending on the particular testing conditions in vitro, Polytrim® was slowly fungicidal, and the activity could be attributed to both PMB and BAK. Fungicidal activity was species-, contact time-, and concentration dependent (FIG. 1A). For *C. albicans*, longer times (60-120 min) were required to cause a ≥1-2 log reduction in viable cells (data not shown). A small amount of activity was detectable after brief contact (≤15 min; <10-fold reduction). PMB and BAK individually, were comparable to the commercially prepared Polytrim®, whereas TMP as a sole agent had no effect within 120 min. When diluted 10-fold, neither Polytrim® nor its components caused detectable killing within 120 min (FIG. 1B). Full strength Polytrim® was most effective against *F. solani* (FIG. 2B), causing a ≥3 log reduction (to below the detection limit) in viable conidia within 1 min, while *A. fumigatus* was the most resistant, requiring at least 15-120 min to achieve 1-3 logs of reduction.

Figure 1C:
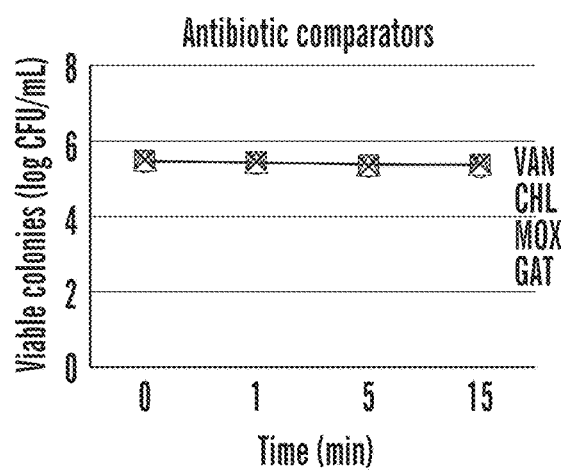
Figure 2A:
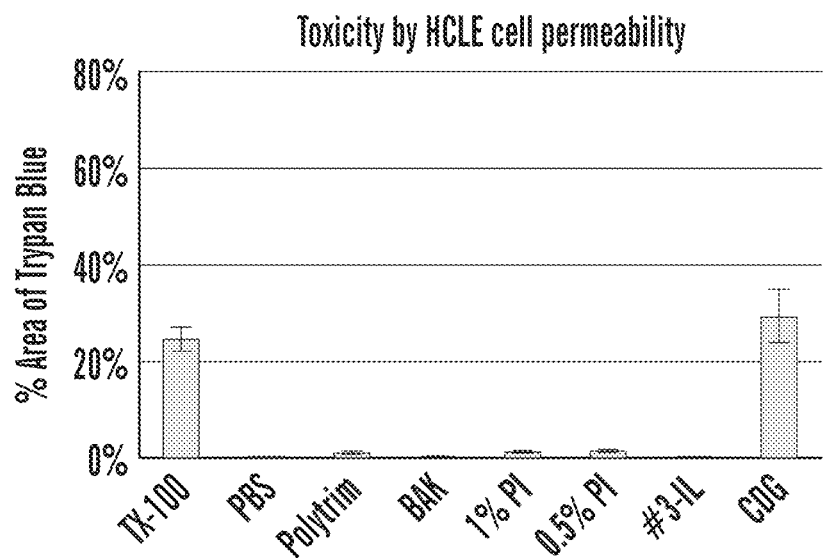
FIGS. 2A-2D demonstrate the fungicidal activity and cytotoxicity of top four candidates.
Figure 2B:
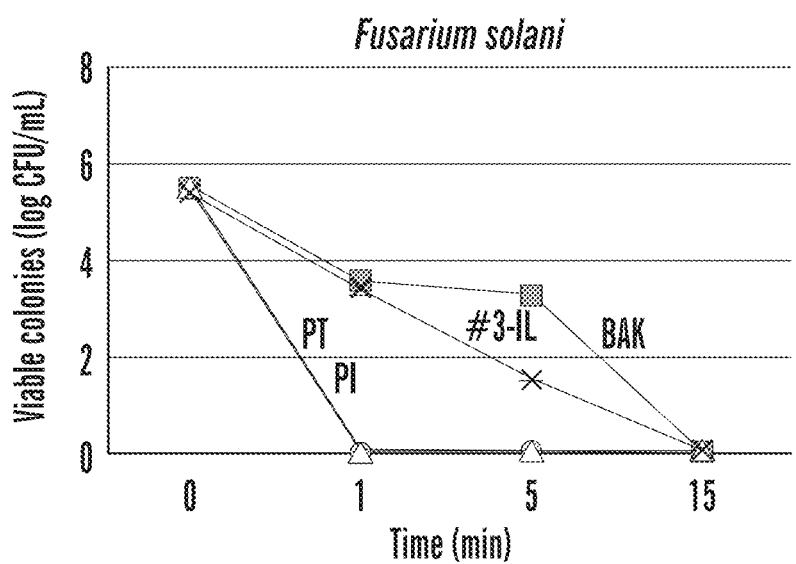
Figure 2C:
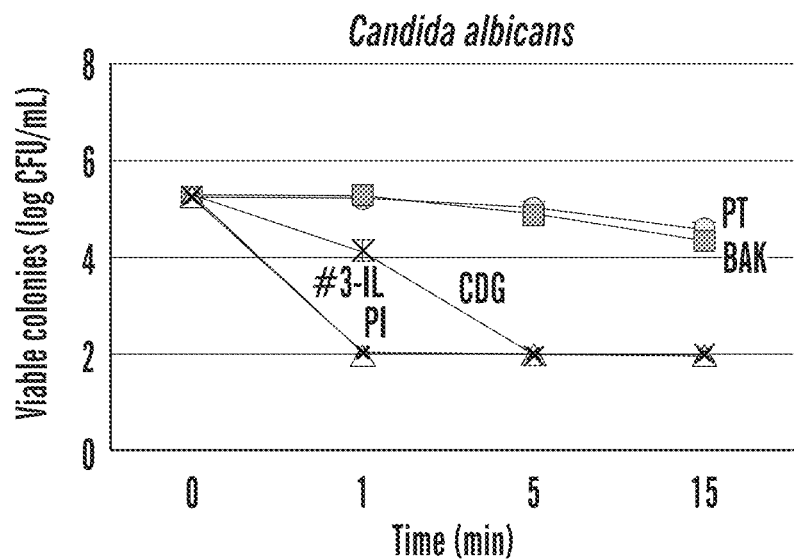
Figure 2D:
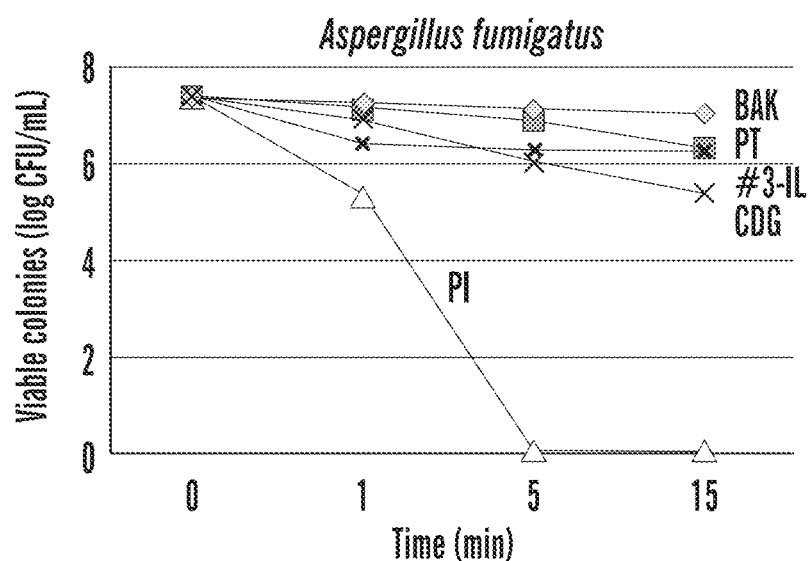

Other commonly used topical antibiotics (0.5% MOX, 0.5% GAT, 0.5% CHL, and 1.4% VAN) prepared without BAK, had no effect against *C. albicans* within 120 min (FIG. 1C). Commercially prepared GAT (Zymaxid®; BAK 0.005%, Allergan; Irvine, Calif.) was as effective as BAK alone in time kill tests with. These results were consistent with findings from previous studies that compared in vitro antifungal activity of antibiotics prepared with and without BAK.[24, 25]

PI Exhibits Rapid and Potent Fungicidal Activity.

PI at concentrations of 0.5-1% exhibited rapid and potent fungicidal activity against all of the tested fungal organisms in vitro (FIGS. 2A-2D), consistent with its well-known broad-spectrum action.[10, 11, 26] At higher concentrations (0.5-1%), PI required less time to kill *C. albicans* compared to the lower (0.01-0.25%), causing a ≥3 log reduction within 1 min, while 0.01-0.1% did not exhibit notable activity (<1 log) within 120 min. These results indicate that povidone iodine, in the range of 0.5-1%, can provide rapid and broad killing of both bacteria and fungi.

Choline-Undecanoate Exhibits Rapid and Potent Fungicidal Activity, and Low Toxicity.

Choline-undecanoate exhibited in vitro fungicidal activity within 1-15 min that was species-, contact time-, and concentration-dependent. Contact with 10 mM of this IL caused a ≥1-4 log reduction in viable *C. albicans*, *F. solani*, and *A. fumigatus* within 1 min (FIGS. 2A-2D).

Cytotoxicity and Efficacy/Toxicity Ratio.

Figure 3:
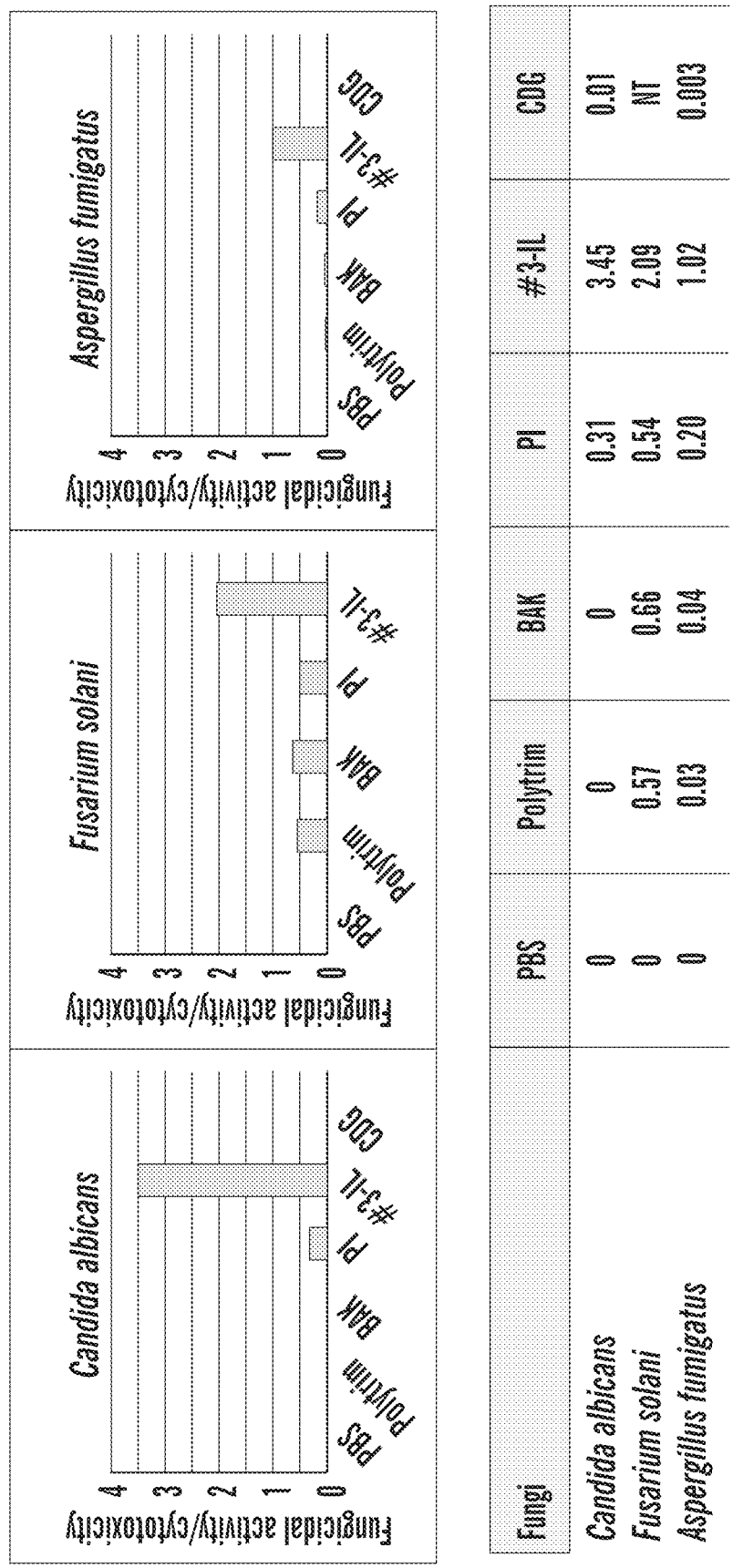
FIG. 3 depicts ratios of fungicidal activity/cytotoxicity. Displayed are the calculated indices for the top candidates. PI and the novel IL had the highest ratios for all three of the tested species. Polytrim® and BAK were similar to PI for *F. solani*, and had the lowest ratio for *C. albicans*. CDG had the lowest ratio for *A. fumigatus*. The ratio is calculated as follows: fungicidal activity/cytotoxicity. Fungicidal activity=# of $\log_{10}$ reduction in viable fungal cells, cytotoxicity=fold-change in Trypan Blue staining relative to the PBS control group (or % stained area for the antimicrobial/PBS) after 1 min contact. PBS=phosphate buffered solution (1×), PT=Polytrim®, BAK=benzalkonium chloride (40 g/mL), PI=povidone iodine (0.5%), #3-IL=ionic liquid (10 mM), CDG=chlorhexidine digluconate (0.05%).
Figure 4:
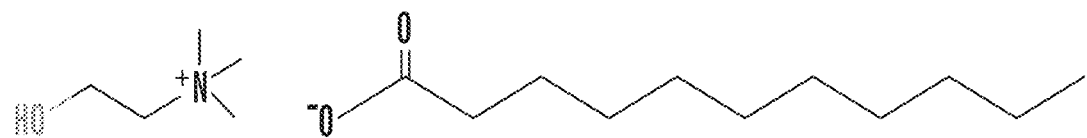
FIG. 4 depicts the chemical formula of the IL. A 1:1 choline ($C_5H_{14}NO$) and undecanoic acid ($C_{11}H_{22}O_2$) ionic liquid at 10 mM in 1×PBS. It is stable at room temperature for months and tolerant of light exposure. The liquid is non-viscous and transparent with a slightly yellow tint. A mild odor is present due to the undecanoate component. (pH 7.2±0.2) Both ingredients are generally recognized as safe (GRAS) by the FDA. Choline is an essential nutrient found in food and various biological pathways involved with cell membrane support, DNA synthesis, neurotransmission, etc. Both choline and undecanoic acid are cost-effective ingredients already being manufactured in large-scale.

The calculated ratios of fungicidal activity and cytotoxicity, shown in FIG. 3, represent their effect against fungi in relation to HCLE cell viability following 1 min of contact. Thus, a higher ratio is indicative of higher safety, and suggests that any immediate damage from topical instillation would be greater against fungal cells than that of host epithelial cells. Theoretically, the cationic component initiates interaction with the cell membrane, allowing for subsequent insertion and/or disruption by the anionic component.[19] FIG. 4 shows the chemical structure of the choline-undecanoate IL used in this study.

Choline-undecanoate IL (10 mM) showed greatest differential killing (ratios >1) for all three fungal species tested, listed in increasing order: *A. fumigatus, F. solani*, and *C. albicans*. In contrast, PI and Polytrim® do not show the same ordering and rank highest for *F. solani*. The fungicidal activity of PI was less variable between the tested species, and ranks second after the novel IL. Polytrim® has a profile that is more species-dependent, ranking the lowest for *C. albicans*, but comparable to that of PI and the novel IL for *F. solani*.

Well-known antiseptic agents, such as CDG and myristamidopropyl dimethylamine (MAPD or Aldox), were also included in the analysis, and found to rank lower than PI. Aldox is an amidoamine antiseptic with reported anti-*acanthamoeba* activity.[27] There are studies comparing its activity to polyhexamethylene biguanide (PHMB) or polyquaternium-1 (PQ-1), which are variations of main ingredients contained in commercial contact lens solutions.[28, 29] In this study, CDG and Aldox exhibited rapid and broad fungicidal activity, but their low ratios derive from their high cytotoxicity to HCLE cells as was measured by post-exposure Trypan blue staining. As such, a low ratio does not necessarily indicate a lack of efficacy, but could also represent a broadly damaging effect for both the host and pathogen cells.

Polytrim®-Treated *C. albicans* and Adhesion to Soft Contact Lenses

Figure 5:
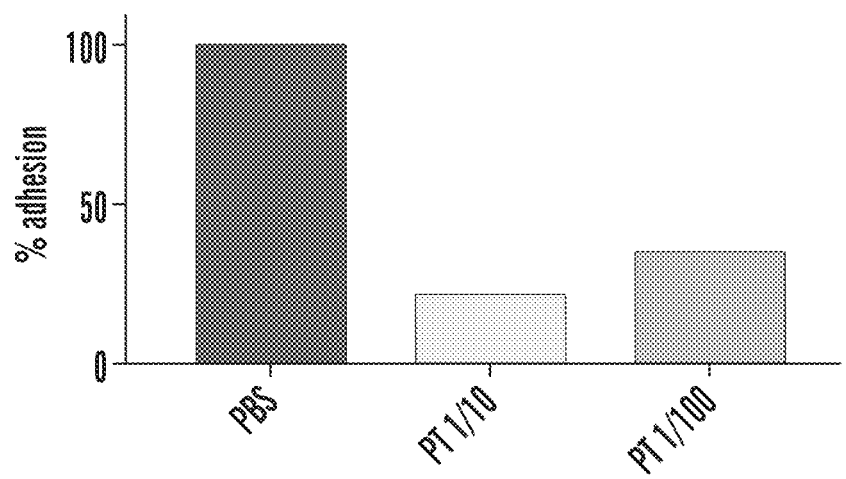
FIG. 5 depicts fungal adhesion. Kontur™ soft contact lenses and Polytrim®: *C. albicans* (ATCC 24433) was pre-treated for 90 min with low concentrations of Polytrim®, and incubated with soft contact lenses after extensive washing to remove traces of the antibiotic. Compared to the non-treated control group, there was a reduction (>50%) in viable colonies recovered from the surface of the soft contact lenses for both the 1/10 and 1/100 strength Polytrim®-treated *Candida* groups. Control=soft contact lenses combined with PBS-treated *C. albicans*. Mean values display the % reduction in number of viable colonies that were adhering to the surface of the soft contact lenses following aerobic incubation at 37° C. The post-sonified solutions containing the soft contact lenses were streaked on Sabouraud dextrose agar to evaluate growth.

Pre-treated *C. albicans* exhibited reduced adherence to the surface of Kontur™ soft contact lenses after overnight incubation at 37° C. Compared to untreated *C. albicans* controls, there was a 77% (1/10 strength Polytrim® pretreatment) and 64% (1/100 strength pretreatment) reduction in adherent fungal cells (FIG. 5). Although 1/10 dilution of Polytrim® did not exhibit fungicidal activity for *C. albicans* in vitro (FIG. 1B), contact with *C. albicans* for 90 min resulted in less fungal cell adhesion on soft contact lenses recommended for extended wear in B-KPro patients following surgery. This difference was also present at the lowest tested concentration (1/100 strength), showing that sub-fungicidal amounts of Polytrim® can prevent fungal adhesion.

Fungal Penetration of Gamma-Irradiated Pig Cornea

Experiments with gamma-irradiated pig corneas showed that they were intrinsically more resistant to penetration by *C. albicans* (ATCC 24433) than to non-treated pig corneas (FIG. 6). Hyphal infiltration was observed as a faint blue pattern (calcofluor white) within the denuded stromal tissue layers. This staining pattern was observed in approximately a half-depth layer of non-treated corneas after 48 hrs of aerobic incubation at 37° C., while it was absent in the gamma-irradiated corneas. Some stiffness of the tissue was also noted in handling the treated corneas, which is consistent with previous findings from another study of gamma-irradiated pig eyes.[30]

Discussion

Surgical replacement of the cornea with a prosthesis is a proven method for restoring vision in eyes for which other therapies either fail or are not possible. Particularly in limited resource countries in warm and humid climates, practical, effective, low toxicity, and inexpensive antifungal prophylaxis regimen after KPro implantation would be of considerable value in extending the utility of this surgical intervention.

Described herein is the evaluation of the possible antifungal effect of antimicrobials that are already in use to prevent bacterial endophthalmitis, including antibiotics and promising antiseptics. Antifungals, which would be too expensive or otherwise impractical to use prophylactically in KPro eyes over a lifetime around the world were not examined.

Based on unfavorable efficacy/toxicity ratio, or cost or stability issues, some of the tested substances can be eliminated outright. Thus, the antibiotics FQ's, VAN, CHL, and TMP, often very effective against bacteria, were found to be ineffective against the fungi tested. The antiseptic CDG, although effective, was too toxic in tests conducted here to be likely practical for years-long prophylaxis.

Remaining candidates include:
1) PMB+BAK in the form of Polytrim®, or equivalent, although when tested in vitro, the effect was weak. However, it has been used for years in large numbers of B-KPro patients with good tolerance. There are hints of antifungal effect sufficient for prophylaxis, even in low doses, and a large-scale field trial in developing countries may be warranted. Thus, it is possible that Polytrim® (or equivalent), one drop once or twice a day, with high compliance, can effectively prevent both bacterial and fungal infections.
2) Of the antiseptics, PI, in concentrations of 0.5-5% has been used safely for various purposes in ophthalmology for decades.[26] A 5% solution is acutely painful when instilled into the eye, but a 1% concentration is well tolerated. It does not select microbes for resistance,[31] and it has some effect on biofilms.[32, 33] To our knowledge, there are only a few reports using PI on a chronic basis after KPro implantation or in blepharitis.[12, 34] However, a prophylactic regime of 1% PI, one drop daily or weekly, could prove useful, with the caveat that prophylaxis be stopped if inflammation should set in. This medication would add a second medication to the patient's regimen (not so for Polytrim®, which would could have a "two-in-one" benefit). 3) Hypochlorous acid (0.01% Avenova®) has been previously tested extensively in our unit and been found to be highly effective against fungi, and easily tolerated.[2] It is FDA-approved for blepharitis and could be an alternative. One drop daily, prophylactically, could be adequate. However, current high cost and some chemical instability could pose limitations.
4) The novel ILs show considerable promise in that their efficacy/toxicity ratio can be very favorable.[17] The choline-undecanoate possesses wide utility as an antimicrobial. This new class of antimicrobial can be a valuable agent for long term, low toxicity, low cost K-pro prophylaxis.

In spite of the weak antifungal effect by Polytrim® and similar drugs in vitro, they are well tested and may provide prophylactic effect as a first line agent. Should the growing experience indicated that greater protection against fungal infection is needed, 1% PI, although somewhat untested for chronic use, could be of value as a secondary line of treatment (a drop a day, or up to 7 days). The availability of these currently approved and inexpensive agents should give other promising drugs time for further development and testing.

Finally, of interest are the observations that treatment with Polytrim® appears to reduce fungal adhesion to soft contact lenses, and that gamma-irradiated pig corneas exhibit substantially more resistance to fungal penetration than non-treated corneas. The latter may be of considerable value since the use of gamma-irradiated carrier tissue for the B-KPro will increase markedly with introduction of pre-assembled KPro-graft combinations, followed by radiation, resulting in a more practical, safer, and more easily stored and shipped product.[35]

A major problem with any microbial prophylaxis in KPro patients has been the need for long-term uninterrupted compliance with the medication to make the outcome safe. The patient must instill a drop into the eye at least once daily—for life—a task that can be difficult to adhere to, especially in resource-poor countries where the vast majority of the corneal blind patients live.

In the longer term, the problem of prophylaxis compliance may be reduced by use of a drug-eluting contact lens (Ciolino), or a device with similar long-term effect that can reliably be placed in the lower conjunctival fornix, or implanted subconjunctivally.[36]

REFERENCES

1. Durand M L and Dohlman C H, Successful prevention of bacterial endophthalmitis in eyes with the Boston keratoprosthesis. *Cornea*, 2009. 28(8):896-901.
2. Odorcic S, Haas W, Gilmore M S, et al., Fungal Infections After Boston Type 1 Keratoprosthesis Implantation: Literature Review and In Vitro Antifungal Activity of Hypochlorous Acid. *Cornea*, 2015. 34(12):1599-605.
3. Odorcic S, Sabeti S, Haas W, et al., Fungal Infections in Boston Keratoprosthesis Patients: Lessons Learned and Novel Developments on the Horizon. *Semin Ophthalmol*, 2016. 31(1-2):71-84.
4. Barnes S D, Dohlman C H, and Durand M L, Fungal colonization and infection in Boston keratoprosthesis. *Cornea*, 2007. 26(1):9-15.
5. Kim M J, Yu F, and Aldave A J, Microbial keratitis after Boston type I keratoprosthesis implantation: incidence, organisms, risk factors, and outcomes. *Ophthalmology*, 2013. 120(11):2209-16.
6. Mahmoudi S, Masoomi A, Ahmadikia K, et al., Fungal keratitis: An overview of clinical and laboratory aspects. *Mycoses*, 2018. 61(12):916-930.
7. Liu M Y, Zhang L, Yin X L, et al., Endophthalmitis associated with fungal keratitis and penetrating injuries in North China. *Eur J Ophthalmol*, 2019: 1120672119833896.
8. Iyer G, Srinivasan B, Agarwal S, et al., Keratoprosthesis: Current global scenario and a broad Indian perspective. *Indian J Ophthalmol*, 2018. 66(5):620-629.
9. White J H, Stephens G M, and Cinotti A A, The use of povidone-iodine for treatment of fungi in rabbit eyes. *Ann Ophthalmol*, 1972. 4(10):855-6.

10. Apt L, Isenberg S, Yoshimori R, et al., Chemical preparation of the eye in ophthalmic surgery. III. Effect of povidone-iodine on the conjunctiva. *Arch Ophthalmol,* 1984. 102(5):728-9.
11. Koerner J C, George M J, Kissam E A, et al., Povidone-iodine concentration and in vitro killing time of bacterial corneal ulcer isolates. *Digit J Ophthalmol,* 2018. 24(4): 24-26.
12. Magalhaes F P, do Nascimento H M, Ecker D J, et al., Microbiota evaluation of patients with a Boston type I keratoprosthesis treated with topical 0.5% moxifloxacin and 5% povidone-iodine. *Cornea,* 2013. 32(4):407-11.
13. Pelletier J S, Barone S B, and Capriotii J A, Keratoprosthesis prophylaxis: is it time for a paradigm shift? *Clin Ophthalmol,* 2018. 12:1785-1788.
14. Bergsson G, Arnfinnsson J, Steingrimsson 0, et al., In vitro killing of *Candida albicans* by fatty acids and monoglycerides. *Antimicrob Agents Chemother,* 2001. 45(11):3209-12.
15. Ammendola S, Lembo A, Battistoni A, et al., 10-undecanhydroxamic acid, a hydroxamate derivative of the undecanoic acid, has strong antimicrobial activity through a mechanism that limits iron availability. *FEMS Microbiol Lett,* 2009. 294(1):61-7.
16. Petkovic M, Ferguson J L, Gunaratne H Q N, et al., Novel biocompatible cholinium-based ionic liquids-toxicity and biodegradability. *Green Chemistry,* 2010. 12(4): 643-649.
17. O'Toole G A, Wathier M, Zegans M E, et al., Diphosphonium ionic liquids as broad-spectrum antimicrobial agents. *Cornea,* 2012. 31(7):810-6.
18. Agatemor C, Ibsen K N, Tanner E E L, et al., Ionic liquids for addressing unmet needs in healthcare. *Bioeng Transl Med,* 2018. 3(1):7-25.
19. Ibsen K N, Ma H, Banerjee A, et al., Mechanism of Antibacterial Activity of Choline-Based Ionic Liquids (CAGE). *ACS Biomaterials Science & Engineering,* 2018. 4(7):2370-2379.
20. Behlau I, Martin K V, Martin J N, et al., Infectious endophthalmitis in Boston keratoprosthesis: incidence and prevention. *Acta Ophthalmol,* 2014. 92(7):e546-55.
21. National Committee for Clinical Laboratory Standards, *Performance Standard for Antimicrobial Susceptibility Testing.* 2018, 28th ed: Approved Standard M100: Wayne, Pa.
22. National Committee for Clinical Laboratory Standards, *Reference Method for Broth Dilution Antifungal Susceptibility Testing of Yeasts.* 2002, 2nd ed: Approved Standard M27-A2: Wayne, Pa.
23. Friedlaender M H, Breshears D, Amoozgar B, et al., The dilution of benzalkonium chloride (BAK) in the tear film. *Adv Ther,* 2006. 23(6):835-41.
24. Day S, Lalitha P, Haug S, et al., Activity of antibiotics against *Fusarium* and *Aspergillus. Br J Ophthalmol,* 2009. 93(1):116-9.
25. Alfonso E and Miller D, Impact of 4th generation fluoroquinolones on growth rate and detection time of fungal pathogens. *Invest Ophthalmol,* 2005. 46: E-Abstract 2766.
26. Isenberg S J and Apt L, The ocular application of povidone-iodine. *Community Eye Health,* 2003. 16(46): 30-1.
27. Hughes R, Dart J, and Kilvington S, Activity of the amidoamine myristamidopropyl dimethylamine against keratitis pathogens. *J Antimicrob Chemother,* 2003. 51(6): 1415-8.
28. Codling C E, Maillard J Y, and Russell A D, Aspects of the antimicrobial mechanisms of action of a polyquaternium and an amidoamine. *J Antimicrob Chemother,* 2003. 51(5):1153-8.
29. Huang L C, Salvador-Silva M, and Leang R S, Correlations of In Vitro Assays for Assessing Cytotoxicity and Biocompatibility of Contact Lens Multipurpose Solutions. *Eye Contact Lens,* 2018. 44 Suppl 1:S97-s105.
30. Islam M M, Sharifi R, Mamodaly S, et al., Effects of gamma radiation sterilization on the structural and biological properties of decellularized corneal xenografts. *Acta Biomater,* 2019. 96:330-344.
31. Lanker Klossner B, Widmer H R, and Frey F, Nondevelopment of resistance by bacteria during hospital use of povidone-iodine. *Dermatology,* 1997. 195 Suppl 2:10-3.
32. Sivaraman K R, Hou J H, Chang J H, et al., Scanning Electron Microscopic Analysis of Biofilm Formation in Explanted Human Boston Type I Keratoprostheses. *Cornea,* 2016. 35(1):25-9.
33. Hoekstra M J, Westgate S J, and Mueller S, Povidone-iodine ointment demonstrates in vitro efficacy against biofilm formation. *Int Wound J,* 2017. 14(1):172-179.
34. Pelletier J S, Capriotti K, Stewart K S, et al., Demodex Blepharitis Treated with a Novel Dilute Povidone-Iodine and DMSO System: A Case Report. *Ophthalmol Ther,* 2017. 6(2):361-366.
35. Gonzalez-Andrades M, Sharifi R, Islam M M, et al., Improving the practicality and safety of artificial corneas: Pre-assembly and gamma-rays sterilization of the Boston Keratoprosthesis. *Ocul Surf,* 2018. 16(3):322-330.
36. Robert M C, Frenette M, Zhou C, et al., A Drug Delivery System for Administration of Anti-TNF-alpha Antibody. *Transl Vis Sci Technol,* 2016. 5(2):11.

What is claimed herein is:

1. A method of treating a fungal infection in a subject in need thereof, the method comprising:
   administering to the subject a composition comprising at least one ionic liquid comprising a quaternary ammonium cation and an undecanoic acid anion, wherein the quaternary ammonium cation comprises choline or any one of C1 to C7; and wherein the fungal infection is infectious keratitis and/or endophthalmitis.

2. The method of claim 1, wherein the cation has a molar mass equal to or greater than choline.

3. The method of claim 1, wherein the cation is choline, C1, C6, or C7.

4. The method of claim 1, wherein the ionic liquid comprises a ratio of cation to anion of from 2:1 to 1:10.

5. The method of claim 1, wherein the ionic liquid comprises a ratio of cation to anion of from 2:1 to 1:2.

6. The method of claim 1, wherein the ionic liquid has a cation:anion ratio of 1:1.

7. The method of claim 1, wherein the composition does not comprise an active agent other than the at least one ionic liquid.

8. The method of claim 1, wherein the composition is formulated for ocular administration.

9. The method of claim 1, further comprising one or more additional antifungal agents.

10. The method of claim 9, wherein the one or more additional antifungal agents are selected from the group consisting of:
   Amphotericin B; natamycin; voriconazole; povidone-iodine; hypochlorous acid;
   Chlorhexidine digluconate (CDG); vancomycin (VAN); chloramphenicol (CHL);

polymyxin B (PMB); trimethoprim (TMP); benzalkonium chloride (BAK); and combinations thereof.

11. The method of claim 1, wherein the fungal infection is an ocular fungal infection and the composition is administered to one or both eyes.

12. The method of claim 1, wherein the subject is one who has received a corneal surgery.

13. The method of claim 1, further comprising a first step of performing corneal surgery on one or both eyes of the subject.

14. The method of claim 12, wherein the surgery is artificial cornea surgery.

15. The method of claim 1, wherein the fungal infection is an infection of *Candida, Candida albicans, Candida parapsilosis, Fusarium*, or *Aspergillus*.

16. The method of claim 1, wherein the composition is administered daily.

17. The method of claim 1, wherein the composition is provided in or on a contact lens, a lower conjunctival fornix device, or a subconjunctival device.

* * * * *